US011992022B2

(12) United States Patent
Pianfetti et al.

(10) Patent No.: US 11,992,022 B2

(45) Date of Patent: May 28, 2024

(54) METHODS AND CULTURES TO MANUFACTURE PIZZA CHEESE

(71) Applicant: INTERNATIONAL N&H DENMARK APS, Kongens Lyngby (DK)

(72) Inventors: Mikael Pianfetti, Dangé-Saint-Romain (FR); Fabien Buret, Dangé-Saint-Romain (FR); Annie Mornet, Dangé-Saint-Romain (FR)

(73) Assignee: INTERNATIONAL N&H DENMARK APS, Kongens Lyngby (DK)

( * ) Notice: Subject to any disclaimer, the term of this patent is extended or adjusted under 35 U.S.C. 154(b) by 0 days.

(21) Appl. No.: 17/289,080

(22) PCT Filed: Oct. 30, 2019

(86) PCT No.: PCT/EP2019/079613

§ 371 (c)(1), (2) Date: Jun. 9, 2023

(87) PCT Pub. No.: WO2020/089279

PCT Pub. Date: May 7, 2020

(65) Prior Publication Data

US 2022/0000135 A1 Jan. 6, 2022

(30) Foreign Application Priority Data

Oct. 30, 2018 (EP) .................................... 18203296

(51) Int. Cl.

*A23C 19/032* (2006.01)
*A23C 19/05* (2006.01)

(Continued)

(52) U.S. Cl.

CPC .......... *A23C 19/0323* (2013.01); *A23C 19/05* (2013.01); *A23C 19/0684* (2013.01);

(Continued)

(58) Field of Classification Search

CPC . A23C 19/0323; A23C 19/05; A23C 19/0684; A23C 21/026; C12N 1/205;

(Continued)

(56) References Cited

FOREIGN PATENT DOCUMENTS

| | | | |
|---|---|---|---|
| WO | 9933351 | A1 | 7/1999 |
| WO | 2013160413 | A1 | 10/2013 |
| WO | 2019042881 | A1 | 3/2019 |

OTHER PUBLICATIONS

Baskaran et al., Galactose concentration in Pizza cheese prepared by three different culture techniques, vol. 56, No. 4 Nov. 2003 International Journal of Dairy Technology. (Year: 2003).*

(Continued)

*Primary Examiner* — Brent T O'Hern

(57) ABSTRACT

The application is directed to a method to manufacture pasta-filata cheese based on cultures comprising or consisting of either 1) at least a galactose-positive *Streptococcus thermophilus* strain as defined herein or 2) at least a *Streptococcus thermophilus* strain and a *Lactococcus lactis* strain, and to a stretched curd or cheese produced by this method. The application is also directed to a culture or kit-of-part comprising or consisting of a) a galactose-positive *Streptococcus thermophilus* strain as defined herein, and b) *Lactococcus* strain(s) and/or *Lactobacillus helveticus* strain(s).

7 Claims, 5 Drawing Sheets

(51) Int. Cl.
*A23C 19/068* (2006.01)
*A23C 21/02* (2006.01)
*C12N 1/20* (2006.01)
*C12R 1/225* (2006.01)
*C12R 1/46* (2006.01)

(52) U.S. Cl.
CPC ............ *A23C 21/026* (2013.01); *C12N 1/205* (2021.05); *A23V 2400/147* (2023.08); *A23V 2400/231* (2023.08); *A23V 2400/249* (2023.08); *C12R 2001/225* (2021.05); *C12R 2001/46* (2021.05)

(58) Field of Classification Search
CPC .......... C12R 2001/225; C12R 2001/46; A23Y 2220/39; A23Y 2240/41; A23Y 2240/75
USPC ............................................................ 426/38
See application file for complete search history.

(56) References Cited

OTHER PUBLICATIONS

Guidone et al., Effect of adjuncts on microbiological and chemical properties of Scamorza cheese, Journal of Dairy Science vol. 98 No. 3, 2015. (Year: 2015).*

Anbukkarasi et al., "Production of low browning Mozzarella cheese: Screening and characterization of wild galactose fermenting *Streptococcus thermophilus* strains", International Journal of Advanced Research, vol. 1, Issue 5, 2013, pp. 83-96.

De Vin et al, "Molecular and Biochemical Analysis of the Galactose Phenotype of Dairy *Streptococcus thermophilus* Strains Reveals Four Different Fermentation Profiles", Applied and Environmental Microbiology, vol. 71, No. 7, Jul. 2005, pp. 3659-3667.

Delorme et al, "Emergence of a Cell Wall Protease in the *Streptococcus thermophilus* Population", Applied and Environmental Microbiology, vol. 76, No. 2, Jan. 2010, pp. 451-460.

Delorme et al, "Study of *Streptococcus thermophilus* population on a world-wide and historical collection by a new MLST scheme", International Journal of Food Microbiology, vol. 242, Feb. 2, 2017, pp. 70-81.

Dharmar et al, "Galactose concentration in pizza cheese prepared by three different culture techniques", International Journal of Dairy Technology, vol. 56, Issue 4, Nov. 2003, pp. 229-232.

Guidone et al, "Effect of adjuncts on microbiological and chemical properties of Scamorza cheese", J. Dairy Sci., vol. 98, No. 3, Mar. 2015, pp. 1467-1478.

Ma et al, "Correlating mozzarella cheese properties to its production processes and microstructure quantification", Journal of Food Engineering, vol. 115, Issue 2, Mar. 2013, pp. 154-163.

Maiden, Martin C.J., "Multilocus Sequence Typing of Bacteria", Annual Review of Microbiology, vol. 60, 2006, pp. 561-588.

Moynihan et al., "Effect of standardizing the lactose content of cheesemilk on the properties of low-moisture, part-skim Mozzarella cheese", J. Dairy Sci., vol. 99, No. 10, 2016, pp. 7791-7802.

Oberg et al, "Microstructure of Mozzarella Cheese During Manufacture", Food Structure, vol. 12, 1993, pp. 251-258.

Osaili et al, "Effect of Curd Washing Level on Proteolysis and Functionality of Low-Moisture Mozzarella Cheese Made with Galactose-Fermenting Culture", Journal of Food Science, vol. 75, Issue 5, Jun./Jul. 2010, pp. C406-C412.

Yu et al, "Multilocus sequence typing of *Streptococcus thermophilus* from naturally fermented dairy foods in China and Mongolia", BMC Microbiology, vol. 15, 2015, 13 pages.

International Search Report from PCT App. No. PCT/EP2019/079613 dated Dec. 5, 2019, 4 pages.

* cited by examiner

A

B

A.

B.

A.

B.

A.

B.

METHODS AND CULTURES TO MANUFACTURE PIZZA CHEESE

CROSS-REFERENCE TO RELATED APPLICATIONS

This application is a § 371 U.S. national stage patent application of PCT Patent Application No. PCT/EP2019/079613, filed Oct. 30, 2019, which claims priority to European Patent Application No. 18203296.1, filed Oct. 30, 2018, the contents of each which are hereby incorporated by reference in their entireties.

FIELD OF THE INVENTION

The application is directed to a method to manufacture pasta-filata cheese based on cultures comprising or consisting of either 1) at least a galactose-positive *Streptococcus thermophilus* strain as defined herein or 2) at least a *Streptococcus thermophilus* strain and a *Lactococcus lactis* strain, and to a stretched curd or cheese produced by this method. The application is also directed to a culture or kit-of-part comprising or consisting of a) a galactose-positive *Streptococcus thermophilus* strain as defined herein, and b) *Lactococcus* strain(s) and/or *Lactobacillus helveticus* strain(s).

BACKGROUND TO THE INVENTION

Up to recently, most of the cheese made in United States was American cheese such as cheddar. But since some decades now, Italian-style cheese has become more and more popular, working up from millions to billions of pounds produced each year. Mozzarella is the main representative of these Italian-style cheeses, and is extremely popular as a pizza ingredient (pizza cheese). Thus, since some years the consumption of pizza cheese has overtaken American cheese consumption.

To answer the rapid increase of pizza cheese consumption not only in the United States but also in other parts of the word, cheese manufacturers are under pressure to produce more and more pizza cheese. One way to increase the cheese production—without investing in new manufacturing lines—is to decrease the time of manufacture of pizza cheese. There is therefore a requirement from cheese producers to provide solutions to decrease the time of manufacture of pizza cheese without compromising on cheese quality, and in particular on the stretchability feature of pizza cheese.

In addition, cheese producers are more and more concerned by the possibility of valorizing the whey produced during the cheese manufacture both in financial and environmental terms. However, whey valorization requires that the composition is suitable to the steps of concentration and spray drying, what is known to be especially difficult with pizza cheese whey.

Finally, at the same time, pizza retailers and customers from various countries have expressed their preferences for a pizza cheese having reduced browning after cooking, i.e., with less brown blisters on pizza top. Several studies have shown that the browning observed on pizza after cooking is the result of several factors, including the presence of free oil (impacting the number of blisters), the glucose and galactose concentration, . . . . Anbukkarasi et al. reported that galactose-fermenting (Gal+) *Streptococcus thermophilus* strains can be used to reduce the browning of cheese on pizza; however, these strains still release increasing levels of galactose during incubation (levels increasing with time and being very high at 8 hours after incubation). Therefore, Anbukkarasi et al. reported the need to combine these Gal+*S. thermophilus* strains with other strains known to ferment galactose such as *Lactobacillus helveticus* [international Journal of Advance Research (2013): 1(5): 83-96].

The inventors studied several parameters linked to pizza cheese manufacture and pizza cheese cooking, using 2 cultures: a thermophilic culture, conventionally used in pizza cheese, consisting of galactose-negative *S. thermophilus* strains (represented here by the commercial product SWIFT14) and a mesophilic culture made of *Lactococcus lactis* strains (represented here by the commercial product MC70). They confirmed that using a culture consisting of galactose-negative *S. thermophilus* strains, the pizza cheese contained large quantity of galactose (5.49 g/kg curd representing 86% of the total sugars; FIG. 1 and Table 3) and gave a high browning after cooking (L value of 43; FIG. 3); moreover, the quantity of galactose contained in the whey was high (more than 0.4 g/kg; Table 5) to be optimally valorized. The inventors showed in contrast that using a culture consisting of *Lactococcus lactis* strains (MC70) (used in different cheese technologies than pasta-filata cheese) gave acceptable results in terms of galactose in the curd (0.15 g/kg; FIG. 1 and Table 3), of browning after cooking (L value of 64-69; FIG. 3) and of galactose in the whey (0.26 g/Kg; Table 5); however, the time of manufacturing until a curd suitable for stretching is obtained was too long (about 4.5 hours), such that this culture is not acceptable for pasta-filata cheese producers.

The inventors also tested a combination of *Lactobacillus helveticus* and galactose-negative *S. thermophilus* strains (in a 50%/50% ratio). Though the quantities of lactose and galactose were less than when using the SWIFT14 culture, the browning after cooking was still too intense to satisfy the consumers' preferences (data not shown).

None of the solutions studied by the inventors was acceptable to satisfy both the cheese producers and consumers. There is still a need for providing solutions in the manufacture of pasta-filata cheese fulfilling both the requirements of the cheese producers and the preferences of the consumers.

DETAILED DESCRIPTION

Figure 1:
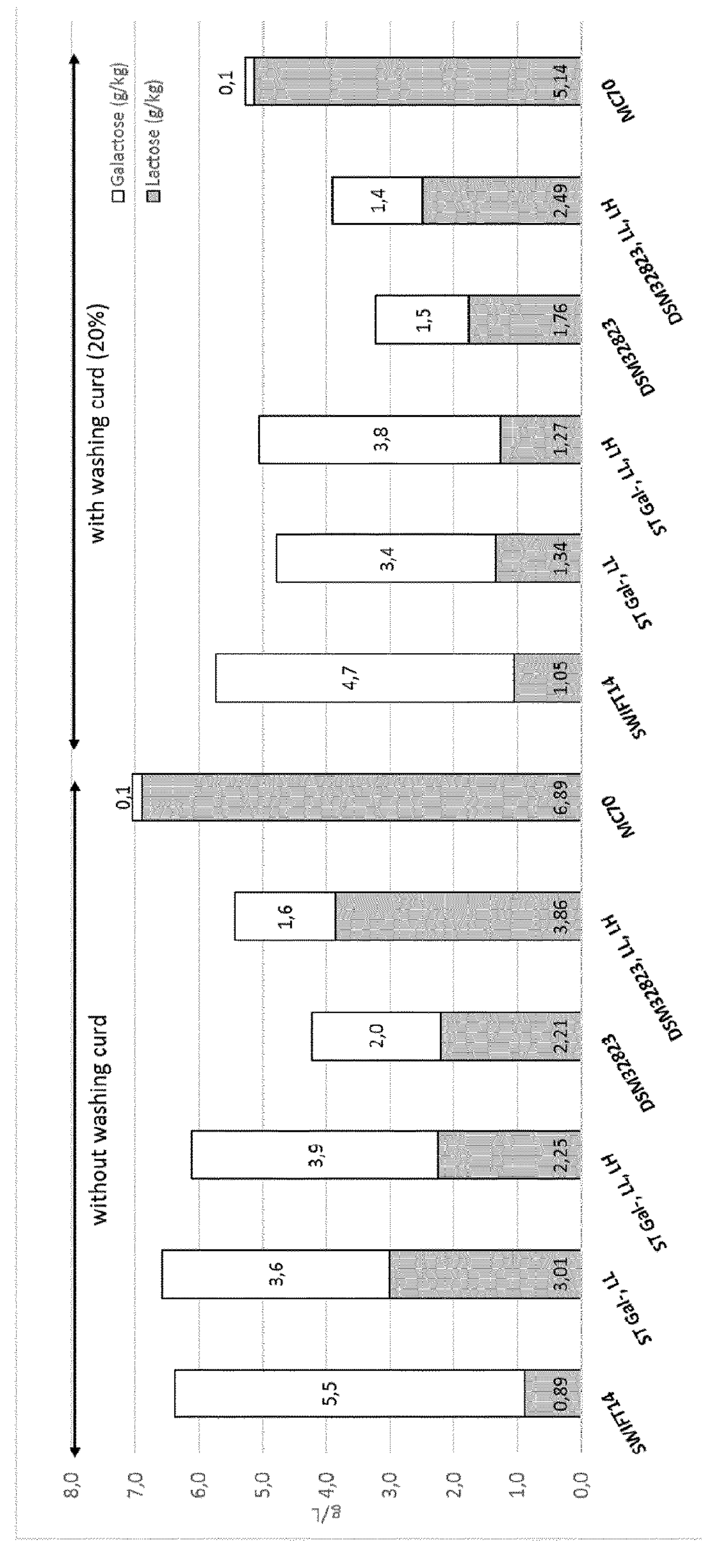
FIG. 1 represents graphs showing the concentration of galactose and glucose in curd (g/kg) using various cultures, with or without curd washing.

With the present invention, the inventors have shown that it is possible to provide solutions fulfilling both the requirements of the cheese producers (time of manufacture, and optionally whey valorisation) and the preferences of the pizza retailers and consumers (low browning on pizza after cooking), by carefully selecting strains and/or designing starter cultures specific to pasta-filata cheese manufacture. Thus, the invention is based on the use of this specific strain(s) or specific starter cultures to manufacture a curd, which is further stretched to obtain pasta-filata cheese (such as pizza cheese).

The invention is directed to a method to manufacture pasta-filata cheese, comprising: a) providing or producing a curd suitable for stretching, wherein said curd is obtained by inoculating and fermenting milk with 1) at least a galactose-positive *Streptococcus thermophilus* strain or 2) at least a *Streptococcus thermophilus* strain and a *Lactococcus lactis* strain, wherein said galactose-positive strain is characterized by:

i. its ability to reach a pH of 5.2 in less than 5 hours, optionally with an average speed of acidification of at least 0.01 upH/min between pH 6.4 and 5.6, when inoculated at 1% (v/v) into a M17 oxoid medium supplemented with galactose 30 g/L and incubated at 43° C., in particular when tested by assay I; and/or ii. either its ability not to excrete galactose, when inoculated at 1% (v/v) into a M17 medium supplemented with 0.5% (wt/wol) of lactose and incubated at 42° C., in particular when tested by assay II or its ability to excrete galactose but to consume the excreted galactose to completion at most 9 hours after being inoculated at 1% (v/v) into a M17 medium supplemented with 0.5% (wt/wol) of lactose and incubated at 42° C., in particular when tested by assay II;

b) stretching the curd of step a) to obtain a stretched curd; and c) manipulating the stretched curd of step b), to finally end up with a pasta-filata cheese.

The invention is also directed to the use of 1) at least a galactose-positive *Streptococcus thermophilus* strain or 2) at least a *Streptococcus thermophilus* strain and at least a *Lactococcus lactis* strain, to manufacture a pasta-filata cheese, wherein said galactose-positive *Streptococcus thermophilus* strain is characterized by:

i. its ability to reach a pH of 5.2 in less than 5 hours, optionally with an average speed of acidification of at least 0.01 upH/min between pH 6.4 and 5.6, when inoculated at 1% (v/v) into a M17 oxoid medium supplemented with galactose 30 g/L and incubated at 43° C., in particular when tested by assay I; and/or ii. either its ability not to excrete galactose, when inoculated at 1% (v/v) into a M17 medium supplemented with 0.5% (wt/wol) of lactose and incubated at 42° C., in particular when tested by assay II or its ability to excrete galactose but to consume the excreted galactose to completion at most 9 hours after being inoculated at 1% (v/v) into a M17 medium supplemented with 0.5% (wt/wol) of lactose and incubated at 42° C., in particular when tested by assay II.

Method or Use to Manufacture Pasta Filata Cheese

The method and use of the invention are intended to manufacture a pasta-filata cheese. As used herein, "pasta-filata cheese" refers to a cheese with a stretched curd. Pasta-filata cheese as defined herein encompasses, but is not limited to, Mozzarella, Provolone, Scarmorza, Cacciocavallo, Kashkaval and pizza cheese derived therefrom (also called low-moisture Mozzarella). In an embodiment, the method and use of the invention are intended to manufacture pizza cheese.

In a first step of the method of the invention, a curd suitable for stretching is either provided or produced.

When the curd is provided, this means that the steps to obtain the curd suitable for stretching (including milk inoculation of lactic acid bacteria as defined herein and fermentation), i.e., the steps which are upstream of providing the curd, are not part of the current method. In this embodiment, the invention is directed to a method to manufacture pasta-filata cheese, comprising:

a) providing a curd suitable for stretching, wherein said curd is previously obtained by inoculating and fermenting milk with 1) at least a galactose-positive *Streptococcus thermophilus* strain or 2) at least a *Streptococcus thermophilus* strain and a *Lactococcus lactis* strain, wherein said galactose-positive strain is characterized by:

i. its ability to reach a pH of 5.2 in less than 5 hours, optionally with an average speed of acidification of at least 0.01 upH/min between pH 6.4 and 5.6, when inoculated at 1% (v/v) into a M17 oxoid medium supplemented with galactose 30 g/L and incubated at 43° C., in particular when tested by assay I; and/or ii. either its ability not to excrete galactose, when inoculated at 1% (v/v) into a M17 medium supplemented with 0.5% (wt/wol) of lactose and incubated at 42° C., in particular when tested by assay II or its ability to excrete galactose but to consume the excreted galactose to completion at most 9 hours after being inoculated at 1% (v/v) into a M17 medium supplemented with 0.5% (wt/wol) of lactose and incubated at 42° C., in particular when tested by assay II;

b) stretching the curd of step a) to obtain a stretched curd; and c) manipulating the stretched curd of step b), to finally end up with a pasta-filata cheese.

Thus, the curd suitable for stretching provided under step a) contains the bacterium or bacteria used for fermenting the milk and obtaining the curd. In an embodiment, the curd suitable for stretching provided under step a) contains, as microorganisms, 1) at least a galactose-positive *Streptococcus thermophilus* strain as defined herein or 2) at least a *Streptococcus thermophilus* strain and a *Lactococcus lactis* strain.

When the curd is produced, this means that the steps to obtain the curd suitable for stretching (including milk inoculation of lactic acid bacteria as defined herein and fermentation) are part of the current method. In this embodiment, the invention is directed to a method to manufacture pasta-filata cheese, comprising:

a1) inoculating milk with 1) at least a galactose-positive *Streptococcus thermophilus* strain or 2) at least a *Streptococcus thermophilus* strain and a *Lactococcus lactis* strain, and optionally with a milk coagulant;

a2) fermenting the inoculated milk of step a1) to obtain a coagulated milk;

a3) cutting the coagulated milk of step a2), heating and stirring, to obtain a mix of curd and whey;

a4) draining the mix of curd and whey of step a3), to obtain a curd suitable for stretching;

b) stretching the curd to obtain a stretched curd; and c) manipulating the stretched curd of step b), to finally end up with a pasta-filata cheese, wherein said galactose-positive strain is characterized by:

i. its ability to reach a pH of 5.2 in less than 5 hours, optionally with an average speed of acidification of at least 0.01 upH/min between pH 6.4 and 5.6, when inoculated at 1% (v/v) into a M17 oxoid medium supplemented with galactose 30 g/L and incubated at 43° C., in particular when tested by assay I; and/or ii. either its ability not to excrete galactose, when inoculated at 1% (v/v) into a M17 medium supplemented with 0.5% (wt/wol) of lactose and incubated at 42° C., in particular when tested by assay I or its ability to excrete galactose but to consume the excreted galactose to completion at most 9 hours after being inoculated at 1% (v/v) into a M17 medium supplemented with 0.5% (wt/wol) of lactose and incubated at 42° C., in particular when tested by assay II.

The curd provided or produced in step a) is characterized by:

its suitability for stretching; and the strain(s) used for producing the curd.

The term"curd" is defined herein as a curd obtained by fermentation, and therefore excludes any curd obtained by chemical acidification. As defined herein, a curd is "suitable for stretching" when the features of the curd (such as but not limited to pH, submicelle dimension) are such that the stretching step enables the curd to adopt fibers characteristics of pasta-filata cheese. These features are well-known in the art and the person skilled in the art knows which curd features are needed at this stage to manufacture a pasta-filtata cheese. In an embodiment, the curd suitable for stretching is characterized by 1 or 2 of following features:

a pH comprised between 4.9 and 5.4, in particular between 5 and 5.3; and/or a submicelle dimension of at least 5 nm, in particular from 5 to 15 nm, in particular from 5 to 10 nm.

In a particular embodiment, the curd suitable for stretching is characterized by a pH comprised between 4.9 and 5.4, in particular between 5 and 5.3.

In a particular embodiment, the curd suitable for stretching is characterized by a submicelle dimension (of at least 5 nm, in particular from 5 to 15 nm, in particular from 5 to 10 nm.

In a particular embodiment, the curd suitable for stretching is characterized by a pH comprised between 4.9 and 5.4, in particular between 5 and 5.3 and a submicelle dimension of at least 5 nm, in particular from 5 to 15 nm, in particular from 5 to 10 nm.

Thus, the curd (provided or produced, in particular produced by steps a1 to a4) is obtained by inoculating milk with the lactic acid bacterium/bacteria as defined herein, and fermenting the inoculated milk.

As defined herein, "milk" means milk from any mammal source, in particular, but not limited to, milk from cow, sheep, goat, buffalo, camel, llama, mare and deer. In an embodiment, the milk is of cow origin. The word "milk" encompasses raw and/or processed milk material that can be subjected to fermentation according to the method of the invention. Thus, the word "milk" includes, solutions/suspensions of any milk, whole or low-fat milk, skim milk, reconstituted milk powder, condensed milk, dried milk, whey or whey permeate. In an embodiment, the milk is previously treated, in particular by standardization, addition of additives [e.g., sugar, sweeteners and/or stabilisers], homogenization and/or heat-treatment [e.g., pasteurization].

The term "inoculation" (or "inoculated" or "inoculating") is used interchangeably with "addition" (or "added" or "adding") and means that the lactic acid bacteria as defined herein are put in contact with the milk, so as to reduce the pH of milk by fermentation (by conversion of carbohydrates into lactic acid) and to produce a coagulated milk. In an embodiment, the inoculation of the lactic acid bacteria defined herein is carried out such as to obtain a coagulated milk.

Thus, according to the invention, the curd is produced by inoculating milk with either 1) at least a galactose-positive *Streptococcus thermophilus* strain as defined herein or 2) at least a *Streptococcus thermophilus* strain and a *Lactococcus lactis* strain.

The expression "at least", when referring to inoculation, means that the milk is inoculated with the mentioned bacterium or mentioned bacteria, and may be inoculated with any other food ingredients suitable to produce the coagulated milk. Food ingredients encompasses 1) microbial food ingredients, i.e., microorganisms such as bacteria, including the bacterium or bacteria described or defined herein) and 2) non-microbial food ingredients. Non-limitating examples of non-microbial food ingredient(s) are boosters, cryoprotectants and lyoprotectants. The expression "other foods ingredients" mean any food ingredient other than the one(s) specifically listed.

As defined herein, the word "strain(s)" means one or more strains, i.e., 1 or more than 1 strains. In an embodiment, the word "strain(s)" means 1, 2, 3, 4, 5, 6, 7, 8, 9 or 10. In an embodiment, the word "strain(s)" means 1, 2, 3, 4 or 5. In an embodiment, the word "strain(s)" means 1, 2 or 3 strains. In an embodiment, the word "strain(s)" means 1 or 2 strains. In an embodiment, the word "strain(s)" means 2 strains. In an embodiment, the word "strain(s)" means 1 strain.

As defined herein, the expression "[non-]microbial food ingredient(s)" means one or more [non-]microbial food ingredients. In an embodiment, the word "[non-]microbial food ingredient(s)" means 1 [non-]microbial food ingredient.

In the embodiment 1), the curd is produced by inoculating milk with at least a galactose-positive *Streptococcus thermophilus* strain (i.e., the milk is inoculated with at least a galactose-positive *Streptococcus thermophilus* strain). The expression "galactose-positive *Streptococcus thermophilus* strain" as defined herein means that the *Streptococcus thermophilus* strain fulfils one of the two following features or the two following features:

i. its ability to reach a pH of 5.2 in less than 5 hours, in particular less than 4 hours, optionally with an average speed of acidification of at least 0.01 upH/min between pH 6.4 and 5.6, when inoculated at 1% (v/v) into a M17 oxoid medium supplemented with galactose 30 g/L and incubated at 43° C., in particular when tested by assay I; and/or ii. either its ability not to excrete galactose, when inoculated at 1% (v/v) into a M17 medium supplemented with 0.5% (wt/wol) of lactose and incubated at 42° C., in particular when tested by assay II or its ability to excrete galactose but to consume the excreted galactose to completion at most 9 hours, in particular at most 8 hours, after being inoculated at 1% (v/v) into a M17 medium supplemented with 0.5% (wt/wol) of lactose and incubated at 42° C., in particular when tested by assay II.

In the present invention, "ability to reach a pH of 5.2 in less than 5 hours, in particular less than 4 hours" means the ability of the strain to decrease the pH of the inoculated medium to a pH of 5.2 in less than 5 hours, in particular less than 4 hours. Thus, the "galactose-positive *Streptococcus thermophilus* strain" as defined herein decreases the pH of the inoculated medium to a pH of 5.2 in less than 5 hours, in particular less than 4 hours, in particular decreases the pH of the inoculated medium to a pH of 5.2 in less than 5 hours, in particular less than 4 hours, when tested by assay I.

In the present invention, "ability not to excrete galactose" means that the strain is not able to excrete any measurable amount of galactose, in particular means that no measurable amount of galactose is detected when tested by assay II. In the present invention, "ability to excrete galactose but to consume the excreted galactose to completion at most 9 hours" means that the strain is able to excrete galactose but to consume the excreted galactose to completion (i.e., to a level below the measurable amount) at most 9 hours after inoculation, in particular means that the strain excretes galactose but consumes the excreted galactose to completion (i.e., to a level below the measurable amount) at most 9 hours after inoculation, when tested by assay II.

In an embodiment, the galactose-positive *Streptococcus thermophilus* strain as defined herein is characterized by its ability to reach a pH of 5.2 in less than 5 hours, optionally with an average speed of acidification of at least 0.01 upH/min between pH 6.4 and 5.6, when inoculated at 1% (v/v) into a M17 oxoid medium supplemented with galactose 30 g/L and incubated at 43° C., in particular when tested by assay I.

In an embodiment, the galactose-positive *Streptococcus thermophilus* strain as defined herein is characterized by its ability to reach a pH of 5.2 in less than 4 hours, optionally with an average speed of acidification of at least 0.01 upH/min between pH 6.4 and 5.6, when inoculated at 1% (v/v) into a M17 oxoid medium supplemented with galactose 30 g/L and incubated at 43° C., in particular when tested by assay I.

In an embodiment, the galactose-positive *Streptococcus thermophilus* strain as defined herein is characterized by its ability not to excrete galactose, when inoculated at 1% (v/v) into a M17 medium supplemented with 0.5% (wt/wol) of lactose and incubated at 42° C., in particular when tested by assay II.

In an embodiment, the galactose-positive *Streptococcus thermophilus* strain as defined herein is characterized by its ability to excrete galactose but to consume the excreted galactose to completion at most 9 hours after being inoculated at 1% (v/v) into a M17 medium supplemented with 0.5% (wt/wol) of lactose and incubated at 42° C., in particular when tested by assay II.

In an particular embodiment, the galactose-positive *Streptococcus thermophilus* strain as defined herein is characterized by its ability to excrete galactose but to consume the excreted galactose to completion at most 8 hours after being inoculated at 1% (v/v) into a M17 medium supplemented with 0.5% (wt/wol) of lactose and incubated at 42° C., in particular when tested by assay II.

In an embodiment, the galactose-positive *Streptococcus thermophilus* strain as defined herein is characterized by its ability to reach a pH of 5.2 in less than 5 hours, in particular less than 4 hours, optionally with an average speed of acidification of at least 0.01 upH/min between pH 6.4 and 5.6, when inoculated at 1% (v/v) into a M17 oxoid medium supplemented with galactose 30 g/L and incubated at 43° C., in particular when tested by assay I, and its ability not to excrete galactose, when inoculated at 1% (v/v) into a M17 medium supplemented with 0.5% (wt/wol) of lactose and incubated at 42° C., in particular when tested by assay II.

In an embodiment, the galactose-positive *Streptococcus thermophilus* strain as defined herein is characterized by its ability to reach a pH of 5.2 in less than 5 hours, in particular less than 4 hours, optionally with an average speed of acidification of at least 0.01 upH/min between pH 6.4 and 5.6, when inoculated at 1% (v/v) into a M17 oxoid medium supplemented with galactose 30 g/L and incubated at 43° C. in particular when tested by assay I and its ability to excrete galactose but to consume the excreted galactose to completion at most 9 hours, in particular at most 8 hours, after being inoculated at 1% (v/v) into a M17 medium supplemented with 0.5% (wt/wol) of lactose and incubated at 42° C., in particular when tested by assay II.

In an embodiment, the galactose-positive *Streptococcus thermophilus* strain as defined herein is the DSM32823 strain deposited at DSMZ on May 29, 2018 or a variant of the DSM32823 strain.

A variant of DSM32823 is herein defined as a *Streptococcus thermophilus* strain presenting at least one mutation, such as the addition, deletion, insertion and/or substitution of at least one nucleotide in its genome as compared to the DSM32823 strain.

In a particular embodiment, the genome sequence of the variant has an identity of at least 99.99% to the genome sequence of the DSM32823 strain. In a particular embodiment, this percentage of identity represents the percentage of the genome sequence present in the genome of the variant and found in the genome of the DSM32823 strain or the percentage of sequences present in the genome of the DSM32823 and found in the mutant strain genome sequence; thus, a variant differing from the DSM32823 strain only by insertion(s) or only by deletion(s) has a genome 100% identical to the genome of the DSM32823 strain, since the whole genome sequence of one strain is totally found in the genome sequence of the other.

In another embodiment, a variant of DSM32823 is characterized in that the sequence of each of several chromosomal loci, defined according to a specific multilocus sequence typing (MLST) scheme, has an identity of least 99% with the sequence of the corresponding chromosomal locus in the DSM32823 strain. Multilocus sequence typing (MLST) analysis is a conventional approach to genotype bacteria based on the sequencing of multiple, distant chromosomal regions of approximately 400 to 600 bp in length (for a review, see "Multilocus sequence typing of bacteria" by Maiden, 2006, *Annu Rev Microbiol.* 60, pp. 561-588). The MLST analysis of *Streptococcus thermophilus* strains can be performed according to at least one of the published MLST schemes (Delorme et al., 2010, *Appl Environ Microbiol.* 76, pp. 451-460; Yu et al., 2015, *BMC Microbiol.* 15:236; Delorme et al., 2017, *Int J Food Microbiol.* 242, pp. 70-81), whose data are available from public international databases (see https://pubmist.org/sthermophilus or http://bigsdb.web.pasteur.fr/*streptococcus*/). In a particular embodiment, a variant of DSM32823 is characterized in that:

- the sequence of each of its 8 chromosomal loci glcK, ddlA, pepO, ilvC, thrS, tkt, pyrE and dnaE, as defined according to the MLST scheme of Delorme et al. 2010 (cited above), has an identity of at least 99%, at least 99.1%, at least 99.2%, at least 99.3%, at least 99.4%, at least 99.5%, at least 99.6%, at least 99.7%, at least 99.8%, at least 99.9%, at least 99.92%, at least 99.94%, at least 99.96%, at least 99.98% or at least 99.99% to the sequence of the corresponding chromosomal locus in the DSM32823 strain; in a particular embodiment, the sequence of each of its 8 chromosomal loci glcK, ddlA, pepO, ilvC, thrS, tkt, pyrE and dnaE, as defined according to the MLST scheme of Delorme et al. 2010 (cited above), is 100% identical to the sequence of the corresponding chromosomal locus in the DSM32823 strain; and/or the sequence of each of its 6 chromosomal loci ddlA, glcK, tkt, ptsl, proA and serB, as defined according to the MLST scheme of Delorme et al. 2017 (cited above), has an identity of at least 99%, at least 99.1%, at least 99.2%, at least 99.3%, at least 99.4%, at least 99.5%, at least 99.6%, at least 99.7%, at least 99.8%, at least 99.9%, at least 99.92%, at least 99.94%, at least 99.96%, at least 99.98% or at least 99.99% to the sequence of the corresponding chromosomal locus in the DSM32823 strain; in a particular embodiment, the sequence of each of its 6 chromosomal loci ddlA, glcK, tkt, ptsl, proA and serB, as defined according to the MLST scheme of Delorme et al. 2017 (cited above), is 100% identical to the sequence of the corresponding chromosomal locus in the DSM32823 strain; and/or the sequence of each of its 10 chromosomal loci carB, clpX, dnaA, murC, murE, pepN, pepX, pyrG, recA and rpoB, as defined according to the MLST scheme of Yu et al. 2015 (cited above), has an identity of at least 99%, at least 99.1%, at least 99.2%, at least 99.3%, at least 99.4%, at least 99.5%, at least 99.6%, at least 99.7%, at least 99.8%, at least 99.9%, at least 99.92%, at least 99.94%, at least 99.96%, at least 99.98% or at least 99.99% to the sequence of the corresponding chromosomal locus in the DSM32823 strain; in a particular embodiment, the sequence of each of its 10 chromosomal loci carB, clpX, dnaA, murC, murE, pepN, pepX, pyrG, recA and rpoB, as defined according to the MLST scheme of Yu et al. 2015 (cited above), is 100% identical to the sequence of the corresponding chromosomal locus in the DSM32823 strain.

Such a variant can be for example:

a natural variant obtained spontaneously from the DSM32823 strain after incubation in a selection medium. A natural variant is thus obtained without any genetic manipulation but only by spontaneous mutation of the strain and selection of the strain in an appropriate medium; or a variant comprising at least one mutation in its genome, said mutation being induced by genetic engineering, for instance by directed mutagenesis or random mutagenesis.

Random mutagenesis can be performed with UV radiations or mutagenic compounds such as nitrous acid, ethylmethanesulfonate, NMethyl-N'-nitro-N-nitrosoguanidine, N-ethyl-N-nitrosourea, acridine orange, proflavine.

In an embodiment, said variant of the DSM32823 strain as defined herein keeps the ability of the DSM32823 strain to reach a pH of 5.2 in less than 5 hours, in particular less than 4 hours, optionally with an average speed of acidification of at least 0.01 upH/min between pH 6.4 and 5.6, when inoculated at 1% (v/v) into a M17 oxoid medium supplemented with galactose 30 g/L and incubated at 43° C., in particular when tested by assay I.

In an embodiment, said variant of the DSM32823 strain as defined herein keeps the ability of the DSM32823 strain not to excrete galactose, when inoculated at 1% (v/v) into a M17 medium supplemented with 0.5% (wt/wol) of lactose and incubated at 42° C., in particular when tested by assay II.

In an embodiment, said variant of the DSM32823 strain as defined herein keeps the ability of the DSM32823 strain to reach a pH of 5.2 in less than 5 hours, in particular less than 4 hours, optionally with an average speed of acidification of at least 0.01 upH/min between pH 6.4 and 5.6, when inoculated at 1% (v/v) into a M17 oxoid medium supplemented with galactose 30 g/L and incubated at 43° C., in particular when tested by assay I and the ability of the DSM32823 strain not to excrete galactose, when inoculated at 1% (v/v) into a M17 medium supplemented with 0.5% (wt/wol) of lactose and incubated at 42° C., in particular when tested by assay II.

Thus, in an embodiment, the milk is inoculated with at least a galactose-positive *Streptococcus thermophilus* strain as defined herein. In an embodiment, the milk is inoculated only with one or more galactose-positive *Streptococcus thermophilus* strain as defined herein. The expression "only with" as defined herein means that no other food ingredient than the one listed is added. In an embodiment, the milk is inoculated only with one galactose-positive *Streptococcus thermophilus* strain as defined herein. In an embodiment, the milk is inoculated with one or more galactose-positive *Streptococcus thermophilus* strain(s) as defined herein and any other food ingredient(s). In an embodiment, the milk is inoculated with one galactose-positive *Streptococcus thermophilus* strain as defined herein and any other food ingredient(s). In an embodiment, the milk is inoculated only with one or more galactose-positive *Streptococcus thermophilus* strain(s) as defined herein and any other microbial food ingredient(s). In an embodiment, the milk is inoculated only with one galactose-positive *Streptococcus thermophilus* strain as defined herein and any other microbial food ingredient(s). In an embodiment, the milk is inoculated only with one or more galactose-positive *Streptococcus thermophilus* strain(s) as defined herein and any non-microbial food ingredient(s). In an embodiment, the milk is inoculated only with one galactose-positive *Streptococcus thermophilus* strain as defined herein and any non-microbial food ingredient(s). As a particular embodiment of any of the embodiments listed above, the one or more galactose-positive *Streptococcus thermophilus* strain(s) is the DSM32823 strain or variant thereof.

In an embodiment, the milk is inoculated with at least a galactose-positive *Streptococcus thermophilus* strain as defined herein, and at least another, preferably one or two, lactic acid bacterium. The expression "lactic acid bacterium/bacteria" encompasses any bacteria of a genus selected in the group consisting of the *Lactococcus* genus, *Streptococcus* genus, *Lactobacillus* genus, *Enterococcus* genus, *Pediococcus* genus, *Leuconostoc* genus, and *Oenococcus* genus. In an embodiment, the at least other, preferably one or two, lactic acid bacterium is a bacterium selected in the group consisting of the *Lactococcus* genus, *Lactobacillus* genus, *Enterococcus* genus, *Pediococcus* genus, *Leuconostoc* genus and *Oenococcus* genus. In an embodiment, the at least other, preferably one or two, lactic acid bacterium is a bacterium of the *Lactococcus lactis* species, including *Lactococcus lactis* subsp. *lactis, Lactococcus lactis* subsp. *cremoris* and *Lactococcus lactis* subsp. *lactis biovar diacetylactis*. In an embodiment, the at least other, preferably one or two, lactic acid bacterium is a bacterium of the *Lactobacillus* genus, in particular of the *Lactobacillus delbrueckii* subsp. *bulgaricus* or *Lactobacillus helveticus* species. In an embodiment, the milk is inoculated only with one or more galactose-positive *Streptococcus thermophilus* strain(s) as defined herein and at least another, preferably one or two, lactic acid bacterium. In an embodiment, the milk is inoculated only with one galactose-positive *Streptococcus thermophilus* strain as defined herein and at least another, preferably one or two, lactic acid bacterium. In an embodiment, the milk is inoculated with one or more galactose-positive *Streptococcus thermophilus* strain(s) as defined herein, at least another, preferably one or two, lactic acid bacterium and any other food ingredient(s). In an embodiment, the milk is inoculated with one galactose-positive *Streptococcus thermophilus* strain as defined herein, at least another, preferably one or two, lactic acid bacterium and any other food ingredient(s). In an embodiment, the milk is inoculated only with one or more galactose-positive *Streptococcus thermophilus* strain(s) as defined herein, at least another, preferably one or two, lactic acid bacterium and any other microbial food ingredient(s). In an embodiment, the milk is inoculated only with one galactose-positive *Streptococcus thermophilus* strain as defined herein, at least another, preferably one or two, lactic acid bacterium and any other microbial food ingredient(s). In an embodiment, the milk is inoculated only with one or more galactose-positive *Streptococcus thermophilus* strain(s) as defined herein, at least another, preferably one or two, lactic acid bacterium and any non-microbial food ingredient(s). In an embodiment, the milk is inoculated only with one galactose-positive *Streptococcus thermophilus* strain as defined herein, at least another, preferably one or two, lactic acid bacterium and any non-microbial food ingredient(s). As a particular embodiment of any of the embodiments listed above, the one or more galactose-positive *Streptococcus thermophilus* strain(s) is the DSM32823 strain or variant thereof.

In an embodiment, the milk is inoculated with at least a galactose-positive *Streptococcus thermophilus* strain as defined herein, and at least another lactic acid bacterium, wherein this other lactic bacterium is not galactose-negative *Streptococcus thermophilus* strain or wherein none of these other lactic acid bacteria are galactose-negative *Streptococcus thermophilus* strains (where a galactose negative bacterium is defined as a *S. thermophilus* strain not able to grow on a medium comprising galactose as the only source of carbohydrates). In an embodiment, the milk is inoculated only with one or more galactose-positive *Streptococcus thermophilus* strain(s) as defined herein and at least another, preferably one or two, lactic acid bacterium, wherein this or these other lactic acid bacterium/bacteria is/are not galactose-negative *Streptococcus thermophilus* strain(s). In an embodiment, the milk is inoculated only with one galactose-positive *Streptococcus thermophilus* strain as defined herein and at least another, preferably one or two, lactic acid bacterium, wherein this or these other lactic acid bacterium/bacteria is/are not galactose-negative *Streptococcus thermophilus* strain(s). In an embodiment, the milk is inoculated with one or more galactose-positive *Streptococcus thermophilus* strain(s) as defined herein, at least another, preferably one or two, lactic acid bacterium and any other food ingredient(s), wherein this or these other lactic acid bacterium/bacteria is/are not galactose-negative *Streptococcus thermophilus* strain(s). In an embodiment, the milk is inoculated with one galactose-positive *Streptococcus thermophilus* strain as defined herein, at least another, preferably one or two, lactic acid bacterium and any other food ingredient(s), wherein this or these other lactic acid bacterium/bacteria is/are not galactose-negative *Streptococcus thermophilus* strain(s). In an embodiment, the milk is inoculated only with one or more galactose-positive *Streptococcus thermophilus* strain(s) as defined herein, at least another, preferably one or two, lactic acid bacterium and any other microbial food ingredient(s), wherein this or these other lactic acid bacterium/bacteria is/are not galactose-negative *Streptococcus thermophilus* strain(s). In an embodiment, the milk is inoculated only with one galactose-positive *Streptococcus thermophilus* strain as defined herein, at least another, preferably one or two, lactic acid bacterium and any other microbial food ingredient(s), wherein this or these other lactic acid bacterium/bacteria is/are not galactose-negative *Streptococcus thermophilus* strain(s). In an embodiment, the milk is inoculated only with one or more galactose-positive *Streptococcus thermophilus* strain(s) as defined herein, at least another, preferably one or two, lactic acid bacterium and any non-microbial food ingredient(s), wherein this or these other lactic acid bacterium/bacteria is/are not galactose-negative *Streptococcus thermophilus* strain(s). In an embodiment, the milk is inoculated only with one galactose-positive *Streptococcus thermophilus* strain as defined herein, at least another, preferably one or two, lactic acid bacterium and any non-microbial food ingredient(s), wherein this or these other lactic acid bacterium/bacteria is/are not galactose-negative *Streptococcus thermophilus* strain(s). As a particular embodiment of any of the embodiments listed above, the one or more galactose-positive *Streptococcus thermophilus* strain(s) is the DSM32823 strain or variant thereof.

In an embodiment, the milk is inoculated with at least a galactose-positive *Streptococcus thermophilus* strain as defined herein and *Lactococcus lactis* strain(s). In an embodiment, the milk is inoculated only with one or more galactose-positive *Streptococcus thermophilus* strain(s) as defined herein and *Lactococcus lactis* strain(s). In an embodiment, the milk is inoculated only with one galactose-positive *Streptococcus thermophilus* strain as defined herein and *Lactococcus lactis* strain(s). In an embodiment, the milk is inoculated with one or more galactose-positive *Streptococcus thermophilus* strain(s) as defined herein, *Lactococcus lactis* strain(s) and any other food ingredient(s). In an embodiment, the milk is inoculated with one galactose-positive *Streptococcus thermophilus* strain as defined herein, *Lactococcus lactis* strain(s) and any other food ingredient(s). In an embodiment, the milk is inoculated only with one or more galactose-positive *Streptococcus thermophilus* strain(s) as defined herein, *Lactococcus lactis* strain(s) and any other microbial food ingredient(s). In an embodiment, the milk is inoculated only with one galactose-positive *Streptococcus thermophilus* strain as defined herein, *Lactococcus lactis* strain(s) and any other microbial food ingredient(s). In an embodiment, the milk is inoculated only with one or more galactose-positive *Streptococcus thermophilus* strain(s) as defined herein, *Lactococcus lactis* strain(s) and any non-microbial food ingredient(s). In an embodiment, the milk is inoculated only with one galactose-positive *Streptococcus thermophilus* strain as defined herein, *Lactococcus lactis* strain(s) and any non-microbial food ingredient(s). As a particular embodiment of any of the embodiments listed above, the one or more galactose-positive *Streptococcus thermophilus* strain(s) is the DSM32823 strain or variant thereof.

In an embodiment, the milk is inoculated with at least a galactose-positive *Streptococcus thermophilus* strain as defined herein, and a *Lactobacillus helveticus* strain. In an embodiment, the milk is inoculated only with one or more galactose-positive *Streptococcus thermophilus* strain(s) as defined herein and a *Lactobacillus helveticus* strain. In an embodiment, the milk is inoculated only with one galactose-positive *Streptococcus thermophilus* strain as defined herein and a *Lactobacillus helveticus* strain. In an embodiment, the milk is inoculated with one or more galactose-positive *Streptococcus thermophilus* strain(s) as defined herein, a *Lactobacillus helveticus* strain and any other food ingredient(s). In an embodiment, the milk is inoculated with one galactose-positive *Streptococcus thermophilus* strain as defined herein, a *Lactobacillus helveticus* strain and any other food ingredient(s). In an embodiment, the milk is inoculated only with one or more galactose-positive *Streptococcus thermophilus* strain(s) as defined herein, a *Lacto-*

*bacillus helveticus* strain and any other microbial food ingredient(s). In an embodiment, the milk is inoculated only with one galactose-positive *Streptococcus thermophilus* strain as defined herein, a *Lactobacillus helveticus* strain and any other microbial food ingredient(s). In an embodiment, the milk is inoculated only with one or more galactose-positive *Streptococcus thermophilus* strain(s) as defined herein, a *Lactobacillus helveticus* strain and any non-microbial food ingredient(s). In an embodiment, the milk is inoculated only with one galactose-positive *Streptococcus thermophilus* strain as defined herein, a *Lactobacillus helveticus* strain and any non-microbial food ingredient(s). As a particular embodiment of any of the embodiments listed above, the one or more galactose-positive *Streptococcus thermophilus* strain(s) is the DSM32823 strain or variant thereof.

In an embodiment, the milk is inoculated with at least a galactose-positive *Streptococcus thermophilus* strain as defined herein, *Lactococcus lactis* strain(s) and a *Lactobacillus helveticus* strain. In an embodiment, the milk is inoculated only with one or more galactose-positive *Streptococcus thermophilus* strain(s) as defined herein, *Lactococcus lactis* strain(s) and a *Lactobacillus helveticus* strain. In an embodiment, the milk is inoculated only with one galactose-positive *Streptococcus thermophilus* strain as defined herein, *Lactococcus lactis* strain(s) and a *Lactobacillus helveticus* strain. In an embodiment, the milk is inoculated with one or more galactose-positive *Streptococcus thermophilus* strain(s) as defined herein, *Lactococcus lactis* strain(s), a *Lactobacillus helveticus* strain and any other food ingredient(s). In an embodiment, the milk is inoculated with one galactose-positive *Streptococcus thermophilus* strain as defined herein, *Lactococcus lactis* strain(s), a *Lactobacillus helveticus* strain and any other food ingredient(s). In an embodiment, the milk is inoculated only with one or more galactose-positive *Streptococcus thermophilus* strain(s) as defined herein, *Lactococcus lactis* strain(s), a *Lactobacillus helveticus* strain and any other microbial food ingredient(s). In an embodiment, the milk is inoculated only with one galactose-positive *Streptococcus thermophilus* strain as defined herein, *Lactococcus lactis* strain(s), a *Lactobacillus helveticus* strain and any other microbial food ingredient(s). In an embodiment, the milk is inoculated only with one or more galactose-positive *Streptococcus thermophilus* strain(s) as defined herein, *Lactococcus lactis* strain(s), a *Lactobacillus helveticus* strain and any non-microbial food ingredient(s). In an embodiment, the milk is inoculated only with one galactose-positive *Streptococcus thermophilus* strain as defined herein, *Lactococcus lactis* strain(s), a *Lactobacillus helveticus* strain and any non-microbial food ingredient(s). As a particular embodiment of any of the embodiments listed above, the one or more galactose-positive *Streptococcus thermophilus* strain(s) is the DSM32823 strain or variant thereof.

In the embodiment 2), the curd is produced by inoculating milk with at least *Streptococcus thermophilus* strain(s) and *Lactococcus lactis* strain(s) (i.e., the milk is inoculated with at least *Streptococcus thermophilus* strain(s) and *Lactococcus lactis* strain(s)). The expression "*Streptococcus thermophilus* strain" encompasses both galactose-positive *Streptococcus thermophilus* strain(s) as defined herein and other *Streptococcus thermophilus* strain(s) as defined herein. In an embodiment of any combination disclosed below, the *Streptococcus thermophilus* strain(s) combined with *Lactococcus lactis* strain(s) is another *Streptococcus thermophilus* strain(s) as defined herein. In an embodiment of any combination disclosed below, the *Streptococcus thermophilus* strain(s) combined with *Lactococcus lactis* strain(s) is a galactose-negative *Streptococcus thermophilus* strain(s) (i.e., a *S. thermophilus* strain not able to grow on a medium comprising galactose as the only source of carbohydrates).

In an embodiment, the milk is inoculated with at least *Streptococcus thermophilus* strain(s) as defined herein and *Lactococcus lactis* strain(s). In an embodiment, the milk is inoculated only with *Streptococcus thermophilus* strain(s) as defined herein and *Lactococcus lactis* strain(s). In an embodiment, the milk is inoculated only with one *Streptococcus thermophilus* strain as defined herein and *Lactococcus lactis* strain(s). In an embodiment, the milk is inoculated only with *Streptococcus thermophilus* strain(s) as defined herein and one *Lactococcus lactis* strain. In an embodiment, the milk is inoculated only with one *Streptococcus thermophilus* strain as defined herein and one *Lactococcus lactis* strain. In an embodiment, the milk is inoculated with *Streptococcus thermophilus* strain(s) as defined herein, *Lactococcus lactis* strain(s) and any other food ingredient(s). In an embodiment, the milk is inoculated with one *Streptococcus thermophilus* strain as defined herein, *Lactococcus lactis* strain(s) and any other food ingredient(s). In an embodiment, the milk is inoculated with *Streptococcus thermophilus* strain(s) as defined herein, one *Lactococcus lactis* strain and any other food ingredient(s). In an embodiment, the milk is inoculated with one *Streptococcus thermophilus* strain as defined herein, one *Lactococcus lactis* strain and any other food ingredient(s). In an embodiment, the milk is inoculated only with *Streptococcus thermophilus* strain(s) as defined herein, *Lactococcus lactis* strain(s) and any other microbial food ingredient(s). In an embodiment, the milk is inoculated only with one *Streptococcus thermophilus* strain as defined herein, *Lactococcus lactis* strain(s) and any other microbial food ingredient(s). In an embodiment, the milk is inoculated only with *Streptococcus thermophilus* strain(s) as defined herein, one *Lactococcus lactis* strain and any other microbial food ingredient(s). In an embodiment, the milk is inoculated only with one *Streptococcus thermophilus* strain as defined herein, one *Lactococcus lactis* strain and any other microbial food ingredient(s). In an embodiment, the milk is inoculated only with *Streptococcus thermophilus* strain(s) as defined herein, *Lactococcus lactis* strain(s) and any non-microbial food ingredient(s). In an embodiment, the milk is inoculated only with one *Streptococcus thermophilus* strain as defined herein, *Lactococcus lactis* strain(s) and any non-microbial food ingredient(s). In an embodiment, the milk is inoculated only with *Streptococcus thermophilus* strain(s) as defined herein, one *Lactococcus lactis* strain and any non-microbial food ingredient(s). In an embodiment, the milk is inoculated only with one *Streptococcus thermophilus* strain as defined herein, one *Lactococcus lactis* strain and any non-microbial food ingredient(s). As a particular embodiment of any of the embodiments listed above, the *Streptococcus thermophilus* strain(s) is or are other(s) *Streptococcus thermophilus* strain(s) as defined herein. As a particular embodiment of any of the embodiments listed above, the *Streptococcus thermophilus* strain(s) is or are galactose-negative *Streptococcus thermophilus* strain(s) as defined herein.

In an embodiment, the milk is inoculated with at least *Streptococcus thermophilus* strain(s) as defined herein, *Lactococcus lactis* strain(s) and a *Lactobacillus helveticus* strain. In an embodiment, the milk is inoculated only with *Streptococcus thermophilus* strain(s) as defined herein, *Lactococcus lactis* strain(s) and a *Lactobacillus helveticus* strain. In an embodiment, the milk is inoculated only with one *Streptococcus thermophilus* strain as defined herein,

*Lactococcus lactis* strain(s) and a *Lactobacillus helveticus* strain. In an embodiment, the milk is inoculated only with *Streptococcus thermophilus* strain(s) as defined herein, one *Lactococcus lactis* strain and a *Lactobacillus helveticus* strain. In an embodiment, the milk is inoculated only with one *Streptococcus thermophilus* strain as defined herein, one *Lactococcus lactis* strain and a *Lactobacillus helveticus* strain. In an embodiment, the milk is inoculated with *Streptococcus thermophilus* strain(s) as defined herein, *Lactococcus lactis* strain(s), a *Lactobacillus helveticus* strain and any other food ingredient(s). In an embodiment, the milk is inoculated with one *Streptococcus thermophilus* strain as defined herein, *Lactococcus lactis* strain(s), a *Lactobacillus helveticus* strain and any other food ingredient(s). In an embodiment, the milk is inoculated with *Streptococcus thermophilus* strain(s) as defined herein, one *Lactococcus lactis* strain, a *Lactobacillus helveticus* strain and any other food ingredient(s). In an embodiment, the milk is inoculated with one *Streptococcus thermophilus* strain as defined herein, one *Lactococcus lactis* strain, a *Lactobacillus helveticus* strain and any other food ingredient(s). In an embodiment, the milk is inoculated only with *Streptococcus thermophilus* strain(s) as defined herein, *Lactococcus lactis* strain(s), a *Lactobacillus helveticus* strain and any other microbial food ingredient(s). In an embodiment, the milk is inoculated only with one *Streptococcus thermophilus* strain as defined herein, *Lactococcus lactis* strain(s), a *Lactobacillus helveticus* strain and any other microbial food ingredient(s). In an embodiment, the milk is inoculated only with *Streptococcus thermophilus* strain(s) as defined herein, one *Lactococcus lactis* strain, a *Lactobacillus helveticus* strain and any other microbial food ingredient(s). In an embodiment, the milk is inoculated only with one *Streptococcus thermophilus* strain as defined herein, one *Lactococcus lactis* strain, a *Lactobacillus helveticus* strain and any other microbial food ingredient(s). In an embodiment, the milk is inoculated only with *Streptococcus thermophilus* strain(s) as defined herein, *Lactococcus lactis* strain(s), a *Lactobacillus helveticus* strain and any non-microbial food ingredient(s). In an embodiment, the milk is inoculated only with one *Streptococcus thermophilus* strain as defined herein, *Lactococcus lactis* strain(s), a *Lactobacillus helveticus* strain and any non-microbial food ingredient(s). In an embodiment, the milk is inoculated only with *Streptococcus thermophilus* strain(s) as defined herein, one *Lactococcus lactis* strain, a *Lactobacillus helveticus* strain and any non-microbial food ingredient(s). In an embodiment, the milk is inoculated only with one *Streptococcus thermophilus* strain as defined herein, one *Lactococcus lactis* strain, a *Lactobacillus helveticus* strain and any non-microbial food ingredient(s). As a particular embodiment of any of the embodiments listed above, the *Streptococcus thermophilus* strain(s) is or are other(s) *Streptococcus thermophilus* strain(s) as defined herein. As a particular embodiment of any of the embodiments listed above, the *Streptococcus thermophilus* strain(s) is or are galactose-negative *Streptococcus thermophilus* strain(s) as defined herein.

When the milk is inoculated with several food ingredients, such as for example at least the galactose-positive *S. thermophilus* strain as defined herein and non-microbial food ingredient(s) or the combination of *S. thermophilus* and *Lactococcus lactis* strains, optionally with other strain(s) and/or non-microbial food ingredients, these food ingredients can be added as separate food ingredients or as a mixture of food ingredients. When the food ingredients are physically separated, they can be added separately or simultaneously in time during the inoculation step. The expression "mixture of food ingredients", means that the ingredients are previously mixed to form a starter culture (or composition) before their inoculation.

In an embodiment, the milk is inoculated with a starter culture comprising or consisting of one or more (in particular one) galactose-positive *Streptococcus thermophilus* strain as defined herein and *Lactococcus* strain(s) and optionally non-microbial ingredient(s). In an embodiment, the milk is inoculated with a starter culture comprising or consisting of one or more (in particular one) galactose-positive *Streptococcus thermophilus* strain as defined herein, *Lactococcus* strain(s) and a *helveticus* strain, and optionally non-microbial ingredient(s). In an embodiment, the milk is inoculated with a starter culture comprising or consisting of one or more (in particular one) *Streptococcus thermophilus* strain as defined herein and *Lactococcus* strain(s), and optionally non-microbial ingredient(s). In an embodiment, the milk is inoculated with a starter culture comprising or consisting of one or more (in particular one) *Streptococcus thermophilus* strain as defined herein, *Lactococcus* strain(s) and a *Lactobacillus helveticus* strain, and optionally non-microbial ingredient(s).

In an embodiment, when the milk is inoculated with *Streptococcus thermophilus* strain(s) as defined herein and *Lactococcus lactis* strain(s) as the only microbial food ingredients [as separate ingredients or as a mixture of ingredients as defined herein], the amount of inoculated *Lactococcus lactis* strain(s) ranges from 50 to 80% w/w of the total amount of inoculated bacteria and the amount of inoculated *Streptococcus thermophilus* strain(s) ranges from 20 to 50% w/w of the total amount of inoculated bacteria ("total amount" is defined herein as the amount of all the inoculated microbial food ingredients calculated as whole). In a particular embodiment, the amount of inoculated *Lactococcus lactis* strain(s) ranges from 60 to 80% w/w of the total amount of inoculated bacteria and the amount of inoculated *Streptococcus thermophilus* strain(s) ranges from 20 to 40% w/w of the total amount of inoculated bacteria. In a particular embodiment, the amount of inoculated *Lactococcus lactis* strain(s) ranges from 60 to 75% w/w of the total amount of inoculated bacteria and the amount of inoculated *Streptococcus thermophilus* strain(s) ranges from 25 to 40% w/w of the total amount of inoculated bacteria.

In an embodiment, when the milk is inoculated with *Streptococcus thermophilus* strain(s) as defined herein, *Lactococcus lactis* strain(s) and a *Lactobacillus helveticus* strain as the only microbial food ingredients [as separate ingredients or as a mixture of ingredients as defined herein], the amount of inoculated *Lactococcus* strain(s) ranges from 35 to 70% w/w of the total amount of inoculated bacteria, the amount of inoculated *Streptococcus thermophilus* strain(s) ranges from 20 to 60% w/w of the total amount of inoculated bacteria, and the amount of inoculated *Lactobacillus helveticus* strain(s) ranges from 5 to 20% w/w of the total amount of inoculated bacteria. In an embodiment, when the milk is inoculated with other *Streptococcus thermophilus* strain(s) as defined herein, *Lactococcus lactis* strain(s) and a *Lactobacillus helveticus* strain as the only microbial food ingredients [as separate ingredients or as a mixture of ingredients as defined herein], the amount of inoculated *Lactococcus* strain(s) ranges from 50 to 70% w/w of the total amount of inoculated bacteria, the amount of inoculated other *Streptococcus thermophilus* strain(s) ranges from 20 to 40% w/w of the total amount of inoculated bacteria, and the amount of inoculated *Lactobacillus helveticus* strain(s) ranges from 5 to 20% w/w of the total amount of inoculated. In an embodiment, when the milk is inoculated with galactose-positive *Streptococcus thermophilus* strain(s) as defined herein, *Lactococcus lactis* strain(s) and a *Lactobacillus helveticus* strain as the only microbial food ingredients [as separate ingredients or as a mixture of ingredients as defined herein], the amount of inoculated *Lactococcus* strain(s) ranges from 35 to 60% w/w of the total amount of inoculated bacteria, the amount of inoculated galactose-positive *Streptococcus thermophilus* strain(s) ranges from 35 to 60% w/w of the total amount of inoculated bacteria, and the amount of inoculated *Lactobacillus helveticus* strain(s) ranges from 5 to 20% w/w of the total amount of inoculated Whatever the number of strains and the nature (species) of strains and whether they are inoculated separately or as a mixture [all as defined herein], the total amount of inoculated strains is at least $1.10^5$ cfu per g of milk. In an embodiment, the total amount of inoculated strains is selected from the group consisting of at least $1.10^5$, at least $1.10^6$, at least $1.10^7$, at least $1.10^8$, at least $1.10^9$, at least $1.10^{10}$ cfu per ml of milk. In an embodiment, the total amount of inoculated strains ranges from $10^5$ to $10^{10}$ cfu/mL of milk.

Whatever the number of strains, the nature (species) of strains and the level of inoculation of strains [all as defined herein] and whether they are inoculated separately or as a mixture [all as defined herein], this or these strain(s) defined herein can be added into the milk, under any form, such as under frozen, dried, freeze-dried, liquid or solid format, in the form of pellets or frozen pellets, or in the form of a powder or dried powder. In an embodiment, the strain(s) defined herein is(are) added into the milk under liquid form, for example as bulk starter [i.e., a culture previously propagated in a growth medium to obtain the required concentration of inoculation]. In an embodiment, the strain(s) defined herein is(are) added into the milk under the form of concentrates, for example frozen or dried concentrates. In a particular embodiment, the concentration of the strain(s) in the frozen or dried concentrate is in the range of $10^8$ to $10^{12}$ cfu per g of concentrate, and more preferably at least $10^8$, at least $10^9$, at least $10^{10}$, at least $10^{11}$ or at least $10^{12}$ cfu/g of concentrate. In an embodiment, the strain(s) defined herein is(are) added into the milk in a frozen format or in the form of pellets or frozen pellets [as frozen concentrates]. In an embodiment, the strain(s) defined herein is(are) added into the milk under powder form, such as a dried or freeze-dried powder [as dried concentrates]. In an embodiment, the strain(s) defined herein is(are) added into the milk under liquid form as a dilution [e.g. in water or saline solution] of concentrates, such as of frozen or dried concentrates. In an embodiment, the strain(s) defined herein is(are) added into the milk under liquid form obtained after thawing of frozen concentrates.

Any embodiment of the inoculation/addition step defined herein can be combined, and in particular any combination of 2, 3 or 4 of the following embodiments or any combination of the 5 embodiments:

1) inoculation with 1) at least a galactose-positive *Streptococcus thermophilus* strain as defined herein or 2) at least a *Streptococcus thermophilus* strain and a *Lactococcus lactis* strain;
2) number of strain(s) to be inoculated as part of 1) at least a galactose-positive *Streptococcus thermophilus* strain as defined herein or 2) at least a *Streptococcus thermophilus* strain and a *Lactococcus lactis* strain;
3) separate inoculation or inoculation as a mixture;
4) the level of inoculation of strains; and
5) the format of inoculation.

In an embodiment, when producing the curd upstream of step a) or as part of step a (in particular in step a1), a milk coagulant is added into the inoculated milk. In an embodiment, the milk coagulant is added from about 20 minutes to about 45 minutes after addition of the lactic acid bacterium or bacteria.

Any type of milk coagulant suitable for the manufacture of pasta-filata cheese can be used. In an embodiment, the milk coagulant is selected from the group consisting of a coagulant of animal origin, a coagulant of microbial origin and a fermentation-produced coagulant.

In an embodiment, the milk coagulant is a coagulant of animal origin. In an embodiment, the milk coagulant is a calf rennet or a lamb rennet. In a particular embodiment, the milk coagulant is a calf rennet, such as the Carlina® coagulant of DuPont™ Danisco®.

In an embodiment, the milk coagulant is a coagulant of microbial origin. In a particular embodiment, the milk coagulant is a milk coagulant selected from a coagulant of *Rhizomucor miehei*, of *Rhizomucor pusillus* and of *Cryphonectria parasitica*. In an embodiment, the milk coagulant is a milk coagulant selected from a coagulant purified from the fermentation of *Rhizomucor miehei*, of *Rhizomucor pusillus* and of *Cryphonectria parasitica*. In a particular embodiment, the milk coagulant is a milk coagulant selected from a coagulant purified from the fermentation of *Rhizomucor miehei*, such as the Marzyme® coagulant of DuPont™ Danisco®. In a particular embodiment, the milk coagulant is a milk coagulant selected from a coagulant purified from the fermentation of *Cryphonectria parasitica*.

In an embodiment, the milk coagulant is a fermentation-produced coagulant (FPC). In an embodiment, the milk coagulant is a bovine chymosin produced by fermentation of modified yeast or filamentous fungi.

When producing the curd upstream of step a) or as part of step a (in particular in step a2), the inoculated milk is fermented to obtain a coagulated milk. By "fermentation" (or fermenting), it is meant to keep the inoculated milk under conditions enabling lactic acid production and formation of a coagulated milk. In a particular embodiment, the inoculated milk is kept at a temperature between 30 and 42° C., in particular between 35° C. and 39° C.

In an embodiment, the inoculated milk is fermented at a temperature between 30 and 42° C., in particular between 35 and 39° C. In an embodiment, the inoculated milk is fermented between about 15 minutes and about 40 minutes, in particular between about 20 minutes and about 30 minutes. In a particular embodiment, the inoculated milk is fermented at a temperature between 30 and 42° C., in particular between 35 and 39° C. and for a period of time between about 15 minutes and about 40 minutes, in particular between about 20 minutes and about 30 minutes. In a particular embodiment, the inoculated milk is fermented at a temperature between 35 and 39° C., for between about 20 minutes and about 30 minutes.

When producing the curd upstream of step a) or as part of step a (in particular in step a3), the coagulated milk is cut, heated and stirred, to obtain a mix of curd and whey.

In an embodiment, the coagulated milk is cut, in the tank, into cubes, in particular into from 1-$cm^3$ to 8-$cm^3$ cubes. As an example, the cutting step lasts about 10 minutes.

In an embodiment, the cut coagulated milk is stirred and heated, in the tank, at a temperature between 38 and 42° C. In an embodiment, in combination or independently of the previous one directed to temperature, the heating and stirring is carried out until the pH of the whey reaches between 6.1 and 6.3. As an example, the heating and stirring step lasts between 10 and 30 minutes, in particular between 15 and 20 minutes.

When producing the curd upstream of step a) or as part of step a (in particular in step a4), the mix of curd and whey is drained (i.e., the whey is removed) to obtain a curd suitable for stretching as defined herein. In an embodiment, the mix of curd and whey is drained at a temperature between 38 and 42° C. The mix of curd and whey is typically drained on a draining table. As an example, the draining step lasts between 2 hours and 2.5 hours.

In step b) of the methods of the invention, the curd (provided or produced) is stretched, to obtain a stretched curd. In an embodiment, the curd is stretched in hot water, whey or salt brine or using direct steam injection. In a particular embodiment, the curd is stretched in hot water the temperature of which is between 55 and 85° C., such that the temperature of the curd is around 50-70° C. The stretching curd is a thermo-mechanical treatment of the curd, which is typically carried out using a cooker/stretcher (such as for example but not limited to, the CMT Mozzarella Cooker Stretcher model F94). As an example, the stretching step lasts between 5 and 15 minutes.

In step c) of the methods of the invention, the stretched curd is manipulated to finally end up with a pasta-filata cheese. Conventional steps after the stretching step include one or more of moulding (put into mould), brining (put into brine) and/or cooling.

The methods of the invention as defined herein optionally comprises additional steps:

In an embodiment, the method optionally comprises washing the curd, during the heating and stirring steps. Thus, when heating and stirring the mix of curd and whey (in particular in step a3)), whey from the tank is removed and replaced by hot water (for example at 40° C.) to speed up the removal of the whey from the curd. In an embodiment, the percentage of whey removed and replaced by hot water is selected from the group consisting of 10, 20, 30 and 40%. In an embodiment, the percentage of whey removed and replaced by hot water ranges from 10 to 30%. In an embodiment, 10±3% of whey is removed and replaced by hot water. In an embodiment, 20±5% of whey is removed and replaced by hot water. In an embodiment, 30±5% of whey is removed and replaced by hot water. Thus, in an embodiment, the invention is directed to a method to manufacture pasta-filata cheese, comprising:

- a1) inoculating milk with 1) at least a galactose-positive *Streptococcus thermophilus* strain or 2) at least a *Streptococcus thermophilus* strain and a *Lactococcus lactis* strain, and optionally with a milk coagulant;
- a2) fermenting the inoculated milk of step a1) to obtain a coagulated milk;
- a3) cutting the coagulated milk of step a2), heating, stirring and washing the curd, to obtain a mix of curd and whey;
- a4) draining the mix of curd and whey of step a3), to obtain a curd suitable for stretching.
- b) stretching the curd to obtain a stretched curd; and
- c) manipulating the stretched curd of step b), to finally end up with a pasta-filata cheese, wherein said galactose-positive strain is characterized by:

- i. its ability to reach a pH of 5.2 in less than 5 hours, in particular less than 4 hours, optionally with an average speed of acidification of at least 0.01 upH/min between pH 6.4 and 5.6, when inoculated at 1% (v/v) into a M17 oxoid medium supplemented with galactose 30 g/L and incubated at 43° C., in particular when tested by assay I; and/or
- ii. either its ability not to excrete galactose, when inoculated at 1% (v/v) into a M17 medium supplemented with 0.5% (wt/wol) of lactose and incubated at 42° C., in particular when tested by assay II or its ability to excrete galactose but to consume the excreted galactose to completion at most 9 hours, in particular at most 8 hours, after being inoculated at 1% (v/v) into a M17 medium supplemented with 0.5% (wt/wol) of lactose and incubated at 42° C., in particular when tested by assay II;

In an embodiment, independently or in combination with the previous one, the method optionally comprises, milling the curd into strips before the stretching step. Thus, in an embodiment, the invention is directed to a method to manufacture pasta-filata cheese, comprising:

- a1) inoculating milk with 1) at least a galactose-positive *Streptococcus thermophilus* strain or 2) at least a *Streptococcus thermophilus* strain and a *Lactococcus lactis* strain, and optionally with a milk coagulant;
- a2) fermenting the inoculated milk of step a1) to obtain a coagulated milk;
- a3) cutting the coagulated milk of step a2), heating and stirring, and optionally washing the curd, to obtain a mix of curd and whey;
- a4) draining the mix of curd and whey of step a3), to obtain a curd suitable for stretching a5) milling the curd to obtain strips of curd
- b) stretching the strips of curd to obtain a stretched curd; and
- c) manipulating the stretched curd of step b), to finally end up with a pasta-filata cheese, wherein said galactose-positive strain is characterized by:
  - i. its ability to reach a pH of 5.2 in less than 5 hours, in particular less than 4 hours, optionally with an average speed of acidification of at least 0.01 upH/min between pH 6.4 and 5.6, when inoculated at 1% (v/v) into a M17 oxoid medium supplemented with galactose 30 g/L and incubated at 43° C., in particular when tested by assay I; and/or
  - ii. either its ability not to excrete galactose, when inoculated at 1% (v/v) into a M17 medium supplemented with 0.5% (wt/wol) of lactose and incubated at 42° C., in particular when tested by assay II or its ability to excrete galactose but to consume the excreted galactose to completion at most 9 hours, in particular at most 8 hours, after being inoculated at 1% (v/v) into a M17 medium supplemented with 0.5% (wt/wol) of lactose and incubated at 42° C., in particular when tested by assay II.

In an advantageous embodiment of the method of the invention, the process time between milk inoculation with the lactic acid bacterium or bacteria as defined herein (in particular step a1) and the time a curd suitable for stretching as defined herein is obtained (in particular end of step a4) is less than 5 hours. In an embodiment, this process time is less than 4.5 hours. In an embodiment, this process time is less than 4 hours. In an embodiment combined with any embodiment described above and disclosing a maximal process time, the process time between milk inoculation with the lactic acid bacterium or bacteria as defined herein (in particular step a1) and the time a curd suitable for stretching as defined herein is obtained (in particular end of step a4) is more than 3.5 hours or more than 3.75 hours. This process time applies when the galactose-positive *Streptococcus thermophilus* strain as defined herein is used or when a combination of at least a *Streptococcus thermophilus* strain and a *Lactococcus lactis* strain is used.

Stretched Curd, Pasta-Filata Cheese and Pasta-Filata Cheese Whey

The invention is also directed to a stretched curd or a pasta-filata cheese or a pasta-filata cheese whey comprising 1) at least a galactose-positive *Streptococcus thermophilus* strain or 2) at least a *Streptococcus thermophilus* strain and a *Lactococcus lactis* strain, wherein said galactose-positive strain is characterized by i. its ability to reach a pH of 5.2 in less than 5 hours, in particular less than 4 hours, optionally with an average speed of acidification of at least 0.01 upH/min between pH 6.4 and 5.6, when inoculated at 1% (v/v) into a M17 oxoid medium supplemented with. galactose 30 g/L and incubated at 43° C., in particular when tested by assay I; and/or ii. either its ability not to excrete galactose, when inoculated at 1% (v/v) into a M17 medium supplemented with 0.5% (wt/wol) of lactose and incubated at 42° C., in particular when tested by assay II or its ability to excrete galactose but to consume the excreted galactose to completion at most 9 hours, in particular at most 8 hours, after being inoculated at 1% (v/v) into a M17 medium supplemented with 0.5% (wt/wol) of lactose and incubated at 42° C., in particular when tested by assay II.

Both stretched curd or a pasta-filata cheese are characterized by a network of parallel-aligned protein fibres, which can be seen using scanning electron microscopy or confocal laser scanning microscopy (Oberg et al. 1993; Food Structure, 12: 251-258—Ma et al. 2013; Journal of Food Engineering; 115:154-163).

In an embodiment, the stretched curd or pasta-filata cheese of the invention is obtained by any of the methods of the invention as defined herein.

By "pasta-filata cheese whey", it is meant a whey obtained during the manufacture of the stretched curd or pasta-filata cheese of the invention, in particular when implementing the method to manufacture pasta-filata cheese of the invention.

Any embodiments and definitions disclosed in the description of the methods of the invention, including but not limited to, the at least galactose-positive *Streptococcus thermophilus* strain as defined herein, the at least *Streptococcus thermophilus* strain and the *Lactococcus lactis* strain(s), the number of strain(s), the other food ingredients, the other microbial food ingredients, the other non-microbial food ingredients and any combinations thereof, apply similarly to the stretched curd, pasta-filata cheese or pasta-filata cheese whey of the invention.

In an embodiment, the stretched curd, pasta-filata cheese or pasta-filata cheese whey of the invention comprises at least the DSM32823 strain deposited at DSMZ on May 29, 2018 or a variant thereof. Any embodiments disclosed in the description of the methods of the invention, including but not limited to, the DSM32823 strain deposited at DSMZ on May29$^{th}$ 2018 or any variant thereof, apply similarly to the stretched curd, pasta-filata cheese or pasta-filata cheese whey of the invention.

Culture or Kit-of-Part

The invention is also directed to a culture or kit-of-part comprising or consisting of a) a galactose-positive *Streptococcus thermophilus* strain and b) *Lactococcus* strain(s) and/or *Lactobacillus helveticus* strain(s), wherein said galactose-positive strain is characterized by i. its ability to reach a pH of 5.2 in less than 5 hours, in particular less than 4 hours, optionally with an average speed of acidification of at least 0.01 upH/min between pH 6.4 and 5.6, when inoculated at 1% (v/v) into a M17 oxoid medium supplemented with galactose 30 g/L and incubated at 43° C., in particular when tested by assay I; and/or ii. either its ability not to excrete galactose, when inoculated at 1% (v/v) into a M17 medium supplemented with 0.5% (wt/wol) of lactose and incubated at 42° C., in particular when tested by assay II or its ability to excrete galactose but to consume the excreted galactose to completion at most 9 hours, in particular at most 8 hours, after being inoculated at 1% (v/v) into a M17 medium supplemented with 0.5% (wt/wol) of lactose and incubated at 42° C., in particular when tested by assay II.

In an embodiment, the culture or kit-of-part of the invention comprises or consists of a galactose-positive *Streptococcus thermophilus* strain as defined herein and *Lactococcus* strain(s). In an embodiment, the culture or kit-of-part of the invention comprises or consists of a galactose-positive *Streptococcus thermophilus* strain as defined herein and *Lactobacillus helveticus* strain(s). In an embodiment, the culture or kit-of-part of the invention comprises or consists of a galactose-positive *Streptococcus thermophilus* strain as defined herein, *Lactococcus* strain(s) and *Lactobacillus helveticus* strain(s).

Any embodiments and definitions disclosed in the description of the methods of the invention, including but not limited to, the at least galactose-positive *Streptococcus thermophilus* strain, a combination of the at least galactose-positive *Streptococcus thermophilus* strain and *Lactococcus lactis* strain(s), a combination of the at least galactose-positive *Streptococcus thermophilus* strain and *Lactobacillus helveticus* strain(s), a combination of the at least galactose-positive *Streptococcus thermophilus* strain *Lactococcus lactis* strain(s) and *Lactobacillus helveticus* strain(s), the other food ingredients, the other microbial food ingredients, the non-microbial food ingredients and any combinations thereof, apply similarly to the culture or kit-of-part of the invention.

The expression "A culture comprising or consisting of a) a galactose-positive *Streptococcus thermophilus* strain; and b) *Lactococcus* strain(s) and/or *Lactobacillus helveticus* strain(s)" means that the galactose-positive *Streptococcus thermophilus* strain as defined herein and the *Lactococcus* strain(s) and/or *Lactobacillus helveticus* strain(s) are physically mixed together. In an embodiment, the galactose-positive *Streptococcus thermophilus* strain as defined herein and *Lactococcus* strain(s) and/or *Lactobacillus helveticus* strain(s) are in the same box or in the same pouch.

In contrast, the expression "A kit-of-part comprising or consisting of a galactose-positive *Streptococcus thermophilus* strain as defined herein and *Lactococcus* strain(s) and/or *Lactobacillus helveticus* strain(s)" means that the culture of the galactose-positive *Streptococcus thermophilus* strain as defined herein and the *Lactobacillus helveticus* strain(s) culture and/or the *Lactococcus* strain(s) culture are physically separated but intended to be used together. Thus, the culture of the galactose-positive *Streptococcus thermophilus* strain as defined herein and the *Lactobacillus helveticus* strain(s) culture and/or the *Lactococcus* strain(s) culture are in different boxes or sachets. In an embodiment, the culture of the galactose-positive *Streptococcus thermophilus* strain as defined herein and the *Lactobacillus helveticus* strain(s) culture and/or the *Lactococcus* strain(s) culture are under the same format, i.e, are in a frozen format, in the form of pellets or frozen pellets, a powder form, such as a dried or freeze-dried powder.

The galactose-positive *Streptococcus thermophilus* strain, *Lactococcus* strain(s) and/or *Lactobacillus helveticus* strain(s), either as a culture or as a kit-of-part, can be under any form suitable for addition or inoculation to the milk, such as under frozen, dried, freeze-dried, liquid or solid format, in the form of pellets or frozen pellets, or in a powder or dried powder. In an embodiment, the galactose-positive *Streptococcus thermophilus* strain as defined herein and the *Lactobacillus helveticus* strain(s) and/or the *Lactococcus* strain(s) are in a frozen format or in the form of pellets or frozen pellets, in particular contained into one or more box or sachet. In an embodiment, the galactose-positive *Streptococcus thermophilus* strain as defined herein and the *Lactobacillus helveticus* strain(s) and/or the *Lactococcus* strain(s) are under a powder form, such as a dried or freeze-dried powder, in particular contained into one or more box or sachet.

In a particular embodiment, the galactose-positive *Streptococcus thermophilus* strain as defined herein and the *Lactobacillus helveticus* strain(s) and/or the *Lactococcus* strain(s), either as a culture or as a kit-of-part, are in a concentration such that they can be directly added or inoculated into the milk—i.e., without previous propagation—such as frozen or dried concentrate. Thus, whatever the form, the concentration of the galactose-positive *Streptococcus thermophilus* strain as defined herein and of the *Lactobacillus helveticus* strain(s) and/or the *Lactococcus* strain(s) are, each separately, in the range of $10^5$ to $10^{12}$ cfu per g of culture, and more preferably at least $10^6$, at least $10^7$, at least $10^8$, at least $10^9$, at least $10^{10}$, at least $10^{11}$ or at least $10^{12}$ cfu/g of culture. When in the form of frozen or dried concentrate, the concentration of the galactose-positive *Streptococcus thermophilus* strain as defined herein and the *Lactobacillus helveticus* strain(s) and/or the *Lactococcus* strain(s) are, each separately, in the range of $10^8$ to $10^{12}$ cfu/g of frozen concentrate or dried concentrate, and more preferably at least $10^8$, at least $10^9$, at least $10^{10}$, at least $10^{11}$ or at least $10^{12}$ cfu/g of frozen concentrate or dried concentrate.

Any combination of galactose-positive *Streptococcus thermophilus* strain as defined herein and *Lactobacillus helveticus* strain(s) and/or *Lactococcus* strain(s) can be used as long as the galactose-positive *Streptococcus thermophilus* strain is characterized by:

i. its ability to reach a pH of 5.2 in less than 5 hours, in particular less than 4 hours, optionally with an average speed of acidification of at least 0.01 upH/min between pH 6.4 and 5.6, when inoculated at 1% (v/v) into a M17 oxoid medium supplemented with galactose 30 g/L and incubated at 43° C., in particular when tested by assay I; and/or ii. either its ability not to excrete galactose, when inoculated at 1% (v/v) into a M17 medium supplemented with 0.5% (wt/wol) of lactose and incubated at 42° C., in particular when tested by assay II or its ability to excrete galactose but to consume the excreted galactose to completion at most 9 hours, in particular at most 8 hours, after being inoculated at 1% (v/v) into a M17 medium supplemented with 0.5% (wt/wol) of lactose and incubated at 42° C., in particular when tested by assay II.

In an embodiment, the galactose-positive *Streptococcus thermophilus* strain as defined herein is the DSM32823 strain deposited at DSMZ on May 29, 2018 or a variant of the DSM32823 strain as defined herein. Any embodiments disclosed in the description of the methods of the invention, including but not limited to, the DSM32823 strain deposited at DSMZ on May 29, 2018 or any variant thereof, apply similarly to the culture or kit-of-part of the invention.

Production of Cheese Whey with a Decreased Level of Galactose

The invention is also directed to the use of at least a galactose-positive strain to produce a cheese whey which has a galactose concentration decreased as compared to a cheese whey produced using a galactose-negative *Streptococcus thermophilus* culture, wherein said galactose-positive strain is characterized by:

i. its ability to reach a pH of 5.2 in less than 5 hours, optionally with an average speed of acidification of at least 0.01 upH/min between pH 6.4 and 5.6, when inoculated at 1% (v/v) into a M17 oxoid medium supplemented with galactose 30 g/L and incubated at 43° C., in particular when tested by assay I; and/or ii. either its ability not to excrete galactose, when inoculated at 1% (v/v) into a M17 medium supplemented with 0.5% (wt/wol) of lactose and incubated at 42° C., in particular when tested by assay II or its ability to excrete galactose but to consume the excreted galactose to completion at most 9 hours after being inoculated at 1% (v/v) into a M17 medium supplemented with 0.5% (wt/wol) of lactose and incubated at 42° C., in particular when tested by assay II.

By "cheese whey", it is meant a whey obtained during the manufacture of a cheese. In an embodiment, the cheese whey is a pasta-filata cheese whey. In a particular embodiment, the cheese whey is a swiss-type cheese whey such as an emmental whey or maasdam whey.

The expression "galactose-negative *Streptococcus thermophilus* culture" means a culture consisting of one or more galactose-negative *Streptococcus thermophilus* strain(s), such as the CHOOZIT SWIFT14 culture (Danisco DuPont).

The cheese whey produced using at least the galactose-positive strain as defined herein has a galactose concentration which is decreased as compared to the galactose concentration of a cheese whey produced using a galactose-negative *Streptococcus thermophilus* culture [with both cheese wheys produced in the same conditions, with the exception of the strains]. By "decrease" it is meant a galactose concentration (g/kg) which is decreased of at least 20% as compared to the galactose concentration of a cheese whey produced using a galactose-negative *Streptococcus thermophilus* culture. In an embodiment, the galactose concentration (g/kg) is decreased of at least 25%. In an embodiment, the galactose concentration (g/kg) is decreased of at least 30%. In an embodiment, the galactose concentration (g/kg) is decreased of at least 40%. In an embodiment, the galactose concentration (g/kg) is decreased of a range comprised between 20% and 50%. In an embodiment, the galactose concentration (g/kg) is decreased of a range comprised between 30% and 45%. In an embodiment, the galactose concentration (g/kg) is decreased of a range comprised between 30% and 40%. In an embodiment, when the whey is a pasta-filata cheese whey, the galactose concentration (g/kg) is decreased of 30%±5% when the method of manufacture of the pasta-filata cheese does not comprise a curd washing step. In an embodiment, when the whey is a pasta-filata cheese whey, the galactose concentration (g/kg) is decreased of 40%±5% when the method of manufacture of the pasta-filata cheese comprises a curd washing step.

Any embodiments and definitions disclosed in the description of the methods of the invention, including but not limited to, the at least galactose-positive *Streptococcus*

*thermophilus* strain as defined herein, the number of strain(s), the other food ingredients, the other microbial food ingredients, the other non-microbial food ingredients and any combinations thereof, apply similarly to the use to produce a cheese whey with a decreased level of galactose of the invention.

In an embodiment, taken alone or in combination with any embodiments disclosed above (for the type of cheese whey and/or % of decrease), the galactose-positive *Streptococcus thermophilus* strain(s) as defined herein is(are) used together with *Lactococcus* strain(s) and/or *Lactobacillus helveticus* strain(s). In an embodiment, taken alone or in combination with any embodiments disclosed above (for the type of cheese whey and/or % of decrease), the galactose-positive *Streptococcus thermophilus* strain(s) as defined herein is(are) not used together with one or more galactose-negative *Streptococcus thermophilus* strain(s).

In an embodiment, the used galactose-positive *Streptococcus thermophilus* strain is the DSM32823 strain deposited at DSMZ on May29$^{th}$, 2018 or a variant thereof. Any embodiments disclosed in the description of the methods of the invention, including but not limited to, the DSM32823 strain deposited at DSMZ on May 29, 2018 or any variant thereof, apply similarly to the use to produce a cheese whey with a decreased level of galactose of the invention.

Deposit and Expert Solution

The following deposit was made according to the Budapest treaty on the international recognition of the deposit of microorganisms for the purposes of patent procedure.

*Streptococcus thermophilus* strain (DGCC7698) deposited under accession number DSM32823 on May29$^{th}$, 2018, at the DSMZ [Deutsche Sammlung von Mikroorganismen und Zellkulturen GmbH, Inhoffenstrasse 7B, D-38124 Braunschweig—Germany] by DuPont Nutrition Biosciences ApS.

It is requested that the biological material shall be made available only by the issue of a sample to an expert nominated by the requester. In respect to those designations in which a European Patent is sought, a sample of the deposited microorganism will be made available until the publication of the mention of the grant of the European patent or until the date on which application has been refused or withdrawn or is deemed to be withdrawn, only by the issue of such a sample to an expert nominated by the person requesting the sample, and approved either i) by the Applicant and/or ii) by the European Patent Office, whichever applies (Rule 32 EPC).

Various preferred features and embodiments of the present invention will now be described by way of non-limiting examples.

EXAMPLES

Example 1: Selection of Galactose-Positive *S. thermophilus* Based on pH (Assay I)

Assay I is as follows:

- *Streptococcus thermophilus* strains characterized as galactose-positive (i.e., described as able to grow on a medium comprising galactose as the only source of carbohydrates) were grown overnight at 37° C. in M17 supplemented with sucrose 30 g/L;
- the culture was washed (v/v) in tryptone-salt solution (tryptone 1 g/L, NaCl 8.5 g/L) as follows: the culture was centrifuged at 4000 rpm for 5 minutes; the pellet was resuspended in 10 ml of tryptone-salt solution
- the washed culture was inoculated at 1% (v/v) into 150 ml of M17 oxoid supplemented with galactose 30 g/L;
- the inoculated medium was incubated at 43° C. for 24 hours, and its pH monitored using a CINAC system (Alliance Instruments, France; pH electrode Mettler 405 DPAS SC, Toledo, Spain); the pH was measured and recorded every 5 minutes. Using the CINAC v2.07 software, the following parameters were specifically calculated: the time to reach a pH of 5.2 and the slope between pH 6.4 and pH 5.6 (UpH/minute) [Slope pH6.4-5.6].

It is expected that it is not sufficient that the tested strain be able to grow on a galactose medium. In addition, this strain must be able to reach the pH of 5.2 (i.e., more or less the pH of stretching in a process to manufacture pasta-filata cheese) in a minimal time, i.e., to optimally consume the galactose of the medium in a manufacturing time which is industrially acceptable. Thus, by assay I, a galactose-positive *S. thermophilus* strain was considered to be suitable for the invention when:

- reaching a pH of 5.2 in less than 5 hours, when tested by assay I (i.e., decreasing the pH of the inoculated medium to 5.2 in less than 5 hours when tested by assay I); and
- optionally with an average speed of acidification of at least 0.01 upH/min between pH 6.4 and 5.6, when tested by assay I.

The following galactose-positive *S. thermophilus* strains and their respective galactose-negative *S. thermophilus* strains (i.e., *S. thermophilus* strains not able to grow on a medium comprising galactose as the only source of carbohydrates) were tested by assay I:

- the DSM32823 strain is the DGCC7698 strain originating from the DuPont/Danisco collection and deposited at the DSMZ on May29$^{th}$, 2018;
- the DSM22934 strain is the CHCC11976 strain described in patent WO2013/160413, and deposited at the DSMZ on Sep. 8, 2009; this strain bears a C at position −4 of the promoter region of the galK gene (herein the "−4 mutation");
- the DGCC7710 strain is a galactose-negative *S. thermophilus* originating from the DuPont/Danisco collection and deposited at the DSMZ under accession number DSM28255 on Jan. 14, 2014;
- the DGCC7710-15 strain was designed by substituting—in the DCC7710 strain—the nucleotide G by a nucleotide T at position -15 of the promoter region of the galK gene (herein "the -15 mutation");
- the DGCC7710-38 strain was designed by inserting—in the DCC7710 strain—a nucleotide A between positions -37 and -38 of the promoter region of the galK gene (herein "the -38 mutation");
- the 715 strain is a galactose-negative *S. thermophilus* originating from the DuPont/Danisco collection;
- the 715-4 strain was designed by introducing the -4 mutation into the 715 strain;

the 715-15 strain was designed by introducing the -15 mutation into the 715 strain;

the 715-38 strain was designed by introducing the -38 mutation into the 715 strain;

the 176 strain is a galactose-negative *S. thermophilus* originating from the DuPont/Danisco collection;

the 176-4 strain was designed by introducing the -4 mutation into the 176 strain;

the 176-15 strain was designed by introducing the -15 mutation into the 176 strain; and the 176-38 strain was designed by introducing the -38 mutation into the 176 strain.

Table 1 summarizes, for each strain, its galactose-fermenting status, the time to reach a pH of 5.20 and the acidification slope between pH 6.4-pH 5.6.

TABLE 1 acidification kinetics of the tested *S. thermophilus* strains

| Strain | Galactose-fermenting status | pH t = 0 | Time pH 5.20 (min.) | Slope pH 6.4-pH 5.6 (upH/min) |
|---|---|---|---|---|
| DSM32823 | Positive | 6.85 | 222 | 0.0146 |
| DSM22934 | Positive | 6.88 | 430 | 0.0096 |
| DGCC7710 | Negative | 6.86 | >1440 | 0.0025 |
| DGCC7710-15 | Positive | 6.86 | >1440 | 0.0033 |
| DGCC7710-38 | Positive | 6.85 | >1440 | 0.0028 |
| 715 | Negative | 6.86 | >1440 | 0.0050 |
| 715-4 | Positive | 6.85 | >1440 | 0.0031 |
| 715-15 | Positive | 6.85 | >1440 | 0.0044 |
| 715-38 | Positive | 6.88 | >1440 | 0.0035 |
| 176 | Negative | 6.86 | >1440 | 0.0031 |
| 176-4 | Positive | 6.87 | >1440 | 0.0016 |
| 176-15 | Positive | 6.85 | >1440 | 0.0025 |
| 176-38 | Positive | 6.85 | 352 | 0.0074 |

Based on assay I, the only strain able to reach the pH of 5.2 in less than 5 hours was strain DSM32823 (in 222 minutes, i.e., less than 4 hours). This strain has also shown to be very fast between pH 6.4 and 5.6 with a maximal acidification speed of almost 0.015 upH/min. All the other strains, except 2, were not able to reach the pH of 5.2 at 24 hours. However, strains 176-38 and DSM22934 were able to reach the pH of 5.2 in about 6 and 7 hours respectively.

Example 2: Selection of Galactose-Positive *S. thermophilus* Based on Galactose Release (Assay II)

Assay II is as follows:

*S. thermophilus* strains characterized as galactose-positive are grown 12 hours at 42° C. in M17 supplemented with 0.5% (wt/vol) of lactose [1% (v/v) inoculation]; this step is repeated a second time in the same conditions;

the culture is inoculated at 1% (v/v) into a M17 medium supplemented with 0.5% (wt/vol) of lactose, and the inoculated medium is incubated at 42° C. up to 10 hours;

during fermentation, samples are withdrawn every 30 minutes to determine the galactose concentration; samples are centrifuged at 14000×g for 5 minutes, filtered sterilized through Phenex nylon 0.45 μm-pore size×15 mm diameter filters (Phenomenex®) and stored at −20° C. until further analysis; 10 μl of each sample are injected on an Agilent® 1100 HPLC. The elution is done through isocratic mode with pure $H_2O$ at 0.6 ml/min. Sugars are separated in 40 minutes onto a $Pb^{2+}$ ion exchange column (SP0810 Shodex™ 300 mm×8 mm×7 μm). The concentration of galactose (if any) is determined (g/L). Concentration of galactose below 0.05 g/L is considered not measurable.

In addition to or alternatively to the time to reach a pH of 5.2, among galactose positive strains, it is expected that the strains either not able to excrete galactose by assay II or able to excrete galactose into the medium but able to consume it to completion by assay II would offer an interesting behaviour in terms of galactose catabolism into a dairy substrate. Thus, by assay II, a galactose-positive *S. thermophilus* strain is considered to be suitable for the invention when:

no measurable amount of galactose is detected, when tested by assay II; or the strain excretes galactose but consumes the excreted galactose to completion (i.e., to a level below the measurable amount) at most 9 hours after inoculation, when tested by assay II.

Example 3: Manufacture of a Pizza Cheese without Curd Washing

Pizza cheese without curd washing was manufactured as follows:

cow milk (34.25 g of fat, 34.8 g of protein, 139.2 g of dry matter and 359 mg of urea for 1 L of milk) was heat-treated at 74° C. for 1 minute, and cooled to 35° C.

calcium chloride was added at a concentration of 15 g/100 L of milk the pH of the milk was standardized at pH 6.4 by $CO_2$ addition the milk was distributed in 3-liter VATs the cultures to be tested (concentration of $1.10^{10}$-$1.10^{11}$ cfu/g of frozen pellets) were inoculated into the milk in the different VATs the inoculated milk was fermented at 35° C. for 30 minutes, with inoculation of Marzyme (Danisco Dupont reference 90667) at concentration of 2200 IMC/100 L at t=20 minutes, to obtain a coagulated milk at t=1 h, the coagulated milk was cut into cubes of 1-1.5 cm sides, and continuously stirred, and then the temperature was increased to 39° C. in 15 minutes a t=2 h, the curd was molded in mold the diameter of which is 11 cm, and pressed under a weight (1 kg) for 2 minutes; a sample of the whey was removed at this stage to measure the residual sugars (example 9);

the mix of curd and whey was then drained, by placing the mold without weight at 45° C. until the pH of the curd reached 5.2;

the curd was then cooled up to 4° C.;

the curd was then stretched using a cooker stretcher at a rate of 60 rpm with water at 90° C., until the temperature of the stretched curd reached 55° C.

the stretched curd was brined (in a solution of NaCl at 300 g/L) for 30 minutes if needed, the stretched curd was frozen at 18° C. until the measurement of the residual sugars contained in the curd and/or the browning test were carried out (examples 7 and 8)

Example 4: Manufacture of a Pizza Cheese with Curd Washing

Pizza cheese with curd washing (20%) was manufactured as described in example 3 above, except that:

at t=1 h, the coagulated milk was cut into cubes of 1-1.5 cm sides, and continuously stirred, the curd was then washed by substituting 700 ml of whey by 600 ml of water at 40° C. (20%), and then the temperature was then increased to 39° C. in 15 minutes.

Example 5: Strains

The following cultures were tested according to examples 3 and 4 above (12 VATs):

1. commercial culture CHOOZIT MC70 (Danisco Dupont reference: 1259559) consisting of *Lactococcus lactis* strain
2. commercial CHOOZIT SWIFT14 culture (Danisco Dupont reference: 1293083) consisting of galactose-negative *Streptococcus thermophilus* strains
3. non-commercial culture consisting of galactose-negative *Streptococcus thermophilus* strains and *Lactococcus lactis* strain (ST Gal-, LL)
4. non-commercial culture consisting of galactose-negative *Streptococcus thermophilus* strains, *Lactococcus lactis* strain and *Lactobacillus helveticus* strain (ST Gal-, LL, LH)
5. culture consisting of the DSM32823 strain
6. culture consisting of the DSM32823 strain, *Lactococcus lactis* strain and *Lactobacillus helveticus* strain (DSM32823, LL, LH)

Example 6: Time of Manufacture

The time of manufacture corresponding to the period between inoculation (t=0) and the time a curd suitable for stretching is obtained was measured. This time is critical at industrial level for the pizza cheese producers. The data obtained by implementing the manufacturing protocols of examples 3 and 4 using the 6 different cultures are summarized in Table 2.

TABLE 2 time of manufacture of a curd suitable for stretching using different cultures with and without curd washing

| | Culture | Time (minutes) |
|---|---|---|
| Without curd washing | SWIFT14 | 248 |
| | ST Gal−, LL | 248 |
| | ST Gal−, LL, LH | 248 |
| | DSM32823 | 250 |
| | DSM32823, LL, LH | 248 |
| | MC70 | 270 |
| With curd washing (20%) | SWIFT14 | 248 |
| | ST Gal−, LL | 248 |
| | ST Gal−, LL, LH | 248 |
| | DSM32823 | 250 |
| | DSM32823, LL, LH | 248 |
| | MC70 | 270 |

Both the cultures based on the combination of galactose-negative *Streptococcus thermophilus* strains and *Lactococcus lactis* strain and based on the DSM32823 strain enable to obtain a manufacture time similar to the one of the SWIFT14 culture (which is at least 20 minutes less than the MC70 culture).

Example 7: Residual Sugars in Curd after Stretching

A sample of the curd obtained implementing the manufacturing protocols of examples 3 and 4 using the 6 different cultures was obtained and the residual lactose and galactose contained thereof were determined. Curd sample was diluted in sulfuric acid solution, homogenized into liquid cheese and centrifuged. The supernatant was filtrated and injected on HPLC (high-performance-liquid-chromatography). Sugars were separated onto an H+ ion exchange column (ROA Rezex®) 150 mm×7.8 mm×8 μm) column and detected with refractometer. Results of the HPLC measurements are summarized in Table 3 and compared in FIG. 1.

TABLE 3 sugar concentrations in curd using different cultures with and without curd washing

| | Culture | Lactose (g/kg) | Galactose (g/kg) | Total sugars (g/kg) |
|---|---|---|---|---|
| Without curd washing | SWIFT14 | 0.89 | 5.49 | 6.38 |
| | ST Gal−, LL | 3.01 | 3.57 | 6.57 |
| | ST Gal−, LL, LH | 2.25 | 3.86 | 6.11 |
| | DSM32823 | 2.21 | 2.03 | 4.23 |
| | DSM32823, LL, LH | 3.86 | 1.57 | 5.44 |
| | MC70 | 6.89 | 0.15 | 7.04 |
| With curd washing (20%) | SWIFT14 | 1.05 | 4.67 | 5.72 |
| | ST Gal−, LL | 1.34 | 3.44 | 4.78 |
| | ST Gal−, LL, LH | 1.27 | 3.77 | 5.04 |
| | DSM32823 | 1.76 | 1.46 | 3.22 |
| | DSM32823, LL, LH | 2.49 | 1.41 | 3.90 |
| | MC70 | 5.14 | 0.14 | 5.28 |

The two DSM32823-based cultures showed, with or without curd washing, a significant decrease in the concentration of total sugars, as compared to the two controls (SWIFT14 and MC70). These two same cultures also showed an important decrease in the concentration of galactose as compared to SWIFT14 (without curd washing: 1.57 and 2.03 versus 5.49; with curd washing: 1.14 and 1.46 versus 4.67). These results confirm the optimal role of the DSM32823 strain in the consumption of galactose during the pizza cheese manufacture. These also validates at the level of cheese manufacturing the selection done by assay I and assay II.

The addition of *Lactococcus lactis*, and optionally *Lactobacillus helveticus*, to galactose-negative *S. thermophilus* also showed a net significant decrease in the concentration of galactose as compared to SWIFT14, though the concentration of total sugars is more or less maintained as compared to SWIFT14.

Altogether, these results showed that:

the combination of galactose-negative *S. thermophilus* and *Lactococcus lactis*, and optionally *Lactobacillus helveticus* is a suitable solution to decrease the galactose concentration in pizza cheese; and the selection of galactose-positive *S. thermophilus* as defined in the invention (assay I and/or assay II) enables to further improve the decrease of the galactose concentration in pizza cheese.

Example 8: Browning and Luminescence Results

Figure 2:
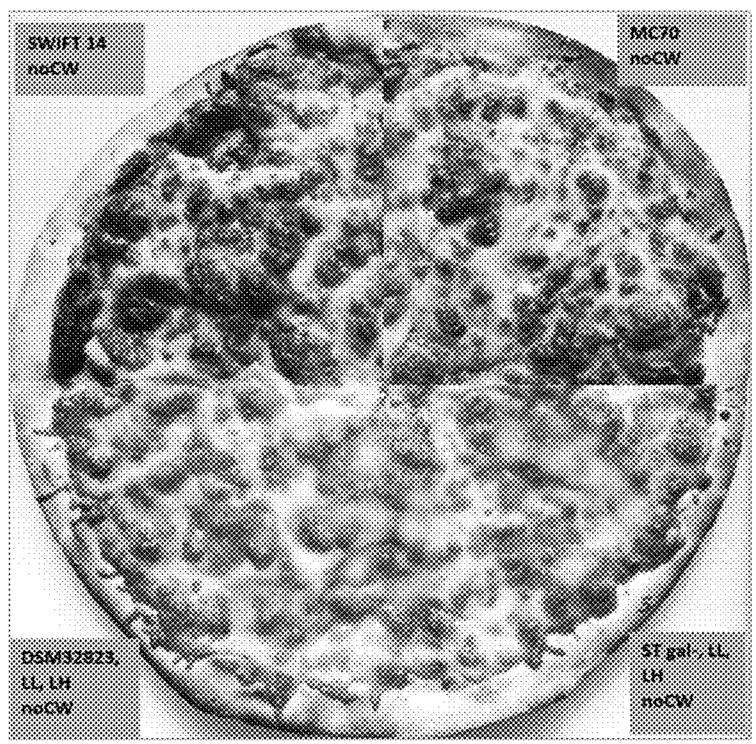
FIG. 2 represents photos of pizza topped and cooked with 30 days-old pizza cheese obtained with various cultures, (A) without or (B) with curd washing.
Figure 2:
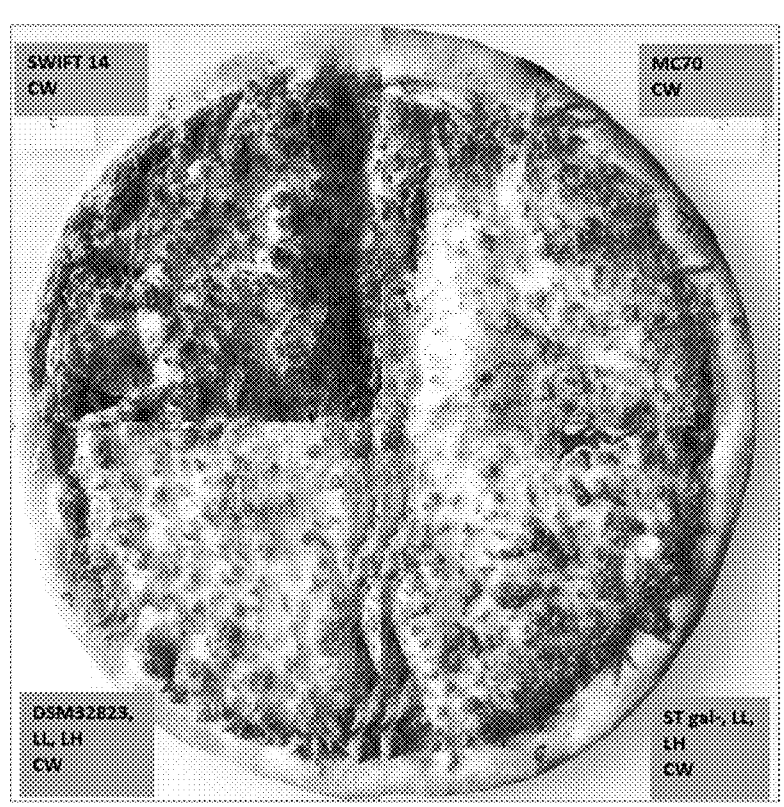

Pizzas were prepared as follows: pizza cheese as prepared in examples 3 and 4 (30-days old cheese matured and stored at 4° C. under foil) was shredded and added on a frozen pizza crust covered of tomato sauce (50 g of pizza cheese was added by quarter of pizza). The pizzas were then baked at 250° C. for 5 min 30 seconds in a Zanolli conveyor pizza oven. FIG. 2 discloses a selection of photographs obtained after pizza cooking.

For each quarter of pizzas, the browning intensity was calculated. A Minolta colorimeter CR-300 was used to measure the color of the pizza surface after cooking. The CIE L*a*b color space (CIELAB), which expresses color as three numerical values—L* for the lightness, a*for the green-red color component and b*for blue-yellow color component—was used. The L value was used to estimate the browning intensity especially the variation of clearness (the lower the L value, the darker the pizza surface). Thus, a pizza was considered as burnt when the L value was below 55. Data of luminescence are presented in FIG. 3. FIG. 4 summarizes the positioning of the different tested cultures in terms of cheese browning.

Figure 3:
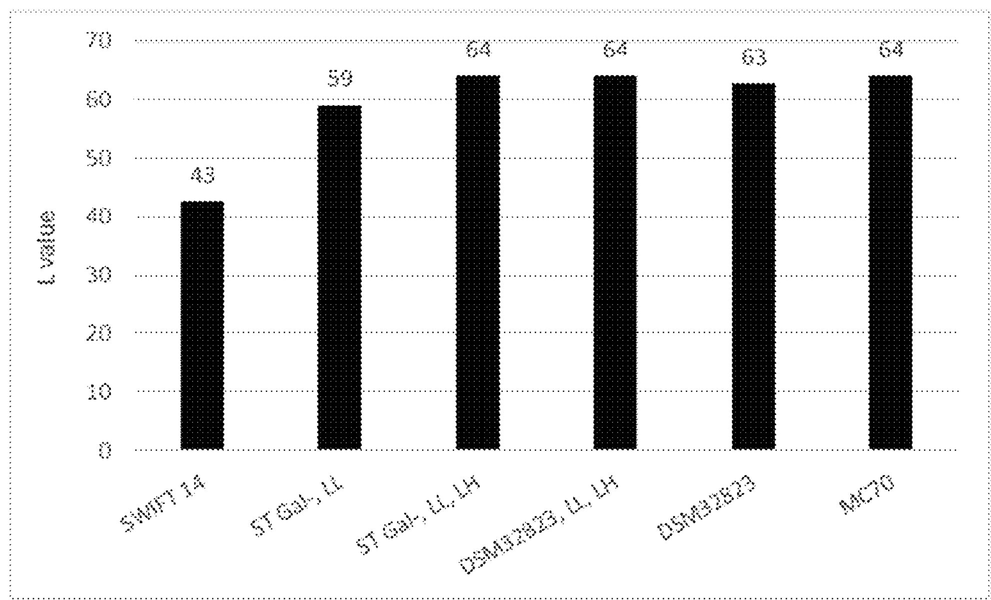
FIG. 3 represents graphs showing the luminescence value (L) of pizza crust topped and cooked with pizza cheese (30 days-old) obtained with various cultures, (A) without or (B) with curd washing.
Figure 3:
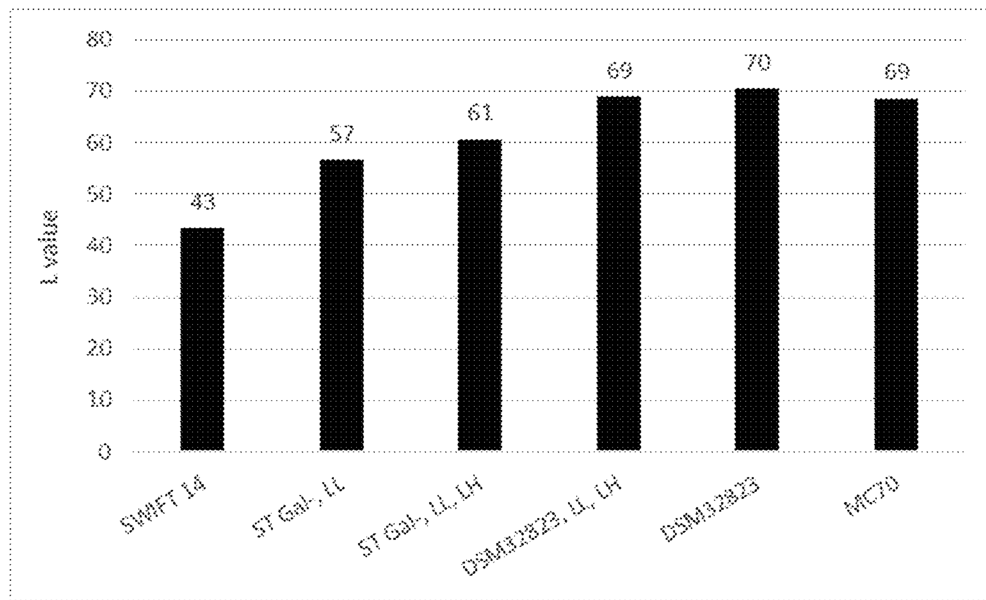
Figure 4:
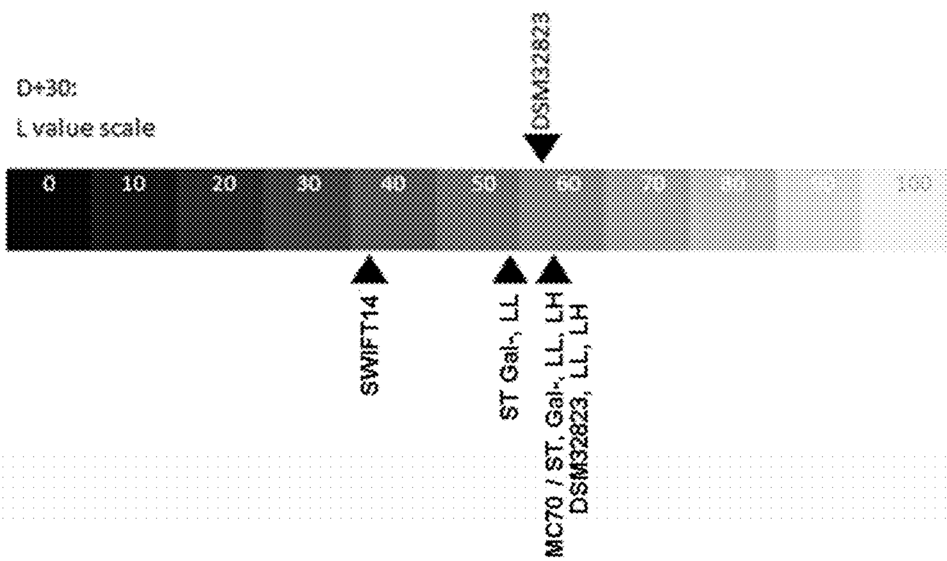
FIG. 4 represents luminescence scale of pizza topped and cooked with 30 days-old pizza cheese obtained with various cultures, (A) without or (B) with curd washing [from the darker (0) to the lighter (100)].
Figure 4:
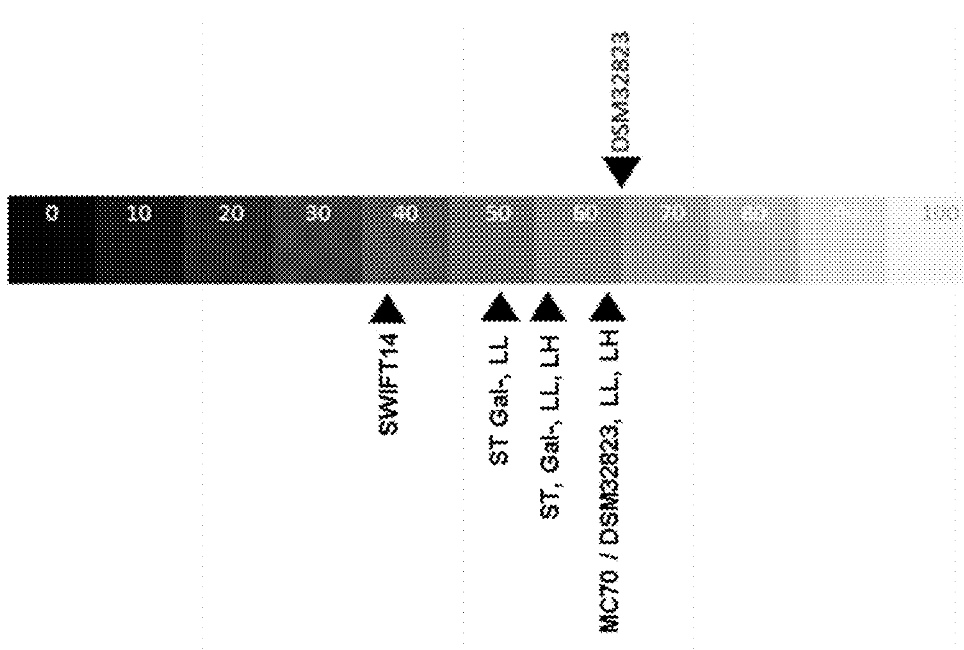

FIG. 3 shows that curd washing has no impact on the browning when using galactose-negative *S. thermophilus* culture (SWIFT14), in contrast to the addition of *Lactococcus lactis* strains (compare SWIFT14 vs ST gal-, LL) or in contrast to the addition of both *Lactococcus lactis* and *Lactobacillus helveticus* strains (compare SWIFT14 vs ST gal-, LL, LH). With cultures comprising both galactose-negative *S. thermophilus* and *Lactococcus lactis* strains, curd washing does not seem to have a significant impact.

The substitution of galactose-negative *S. thermophilus* strains by a galactose-positive *S. thermophilus* strain as defined in the invention (such as DSM32823) clearly shows a significant improvement of the browning reduction: at least 20 points when comparing DSM32823 vs SWIFT14. This significant browning reduction is further improved with curd washing: at least 25 points when comparing DSM32823, LL, LH vs SWIFT14. L values obtained using culture comprising a galactose-positive *S. thermophilus* strain as defined in the invention are closed to, and sometimes even better than L values obtained with MC70 (*Lactococcus lactis* strains only).

Figure 5:
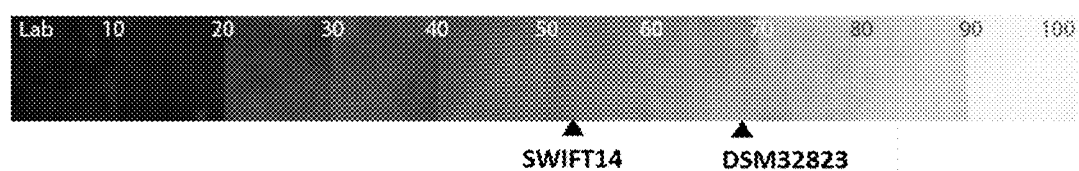
FIG. 5 represents luminescence scale of pizza topped and cooked with 30 days-old pizza cheese (A) or with 60 days-old pizza cheese (B), obtained with 2 different cultures [from the darker (0) to the lighter (100)].
Figure 5:
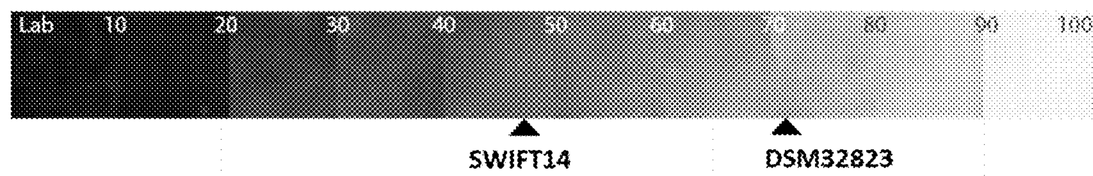

The same experiment was repeated with 30 days old and 60-days old cheese produced with either the galactose-negative *S. thermophilus* culture SWIFT14 or with the DSM32823 strain. The L values (average of 4 calculations) are summarized in Table 4. FIG. 5 shows the positioning of the 2 tested cultures in terms of cheese browning.

TABLE 4

L values calculated for 30 days and 60 days old cheese with 2 different cultures

| | L value with 30 days old cheese | L value with 60 days old cheese |
|---|---|---|
| SWIFT 14 | 52.7 | 47.3 |
| DSM32823 | 67.9 | 71.2 |

Interestingly, the significant browning reduction observed with 30 days old cheese obtained with DSM32823 strain (FIGS. 3 and 4) is maintained for cheese matured and stored for as long as 60 days.

Altogether these results show that more than the galactose-fermenting phenotype of strains, it is either the specific combination of strain species (addition of *Lactococcus lactis* into a galactose-negative *S. thermophilus* culture) or species with specific properties (galactose-positive *S. thermophilus* strain as defined in the invention) which are relevant to significantly reduce the pizza cheese browning.

Thus, the inventors showed that the most significant browning reduction can be obtained using either a culture comprising galactose-negative *S. thermophilus* culture and *Lactococcus lactis* strains or a culture comprising a galactose-positive *S. thermophilus* strain as defined in the invention. Additionally, the inventors showed that the cheese browning reduction is maintained over time (with cheeses matured and stored for at least 60 days) using a galactose-positive *S. thermophilus* strain as defined in the invention. The positioning of the different cultures with respect to pizza browning is shown in FIG. 4 and FIG. 5.

Example 9: Residual Sugars in Whey after Moulding

The whey resulting from the manufacture of pizza cheese is today used as a food ingredient for the high nutritional value of its constituents. However, galactose has been shown to have a negative impact on the crystallization of lactose and the spray drying, two critical steps in the valorization of whey.

During the protocols described in examples 3 and 4, a sample of the whey after moulding was obtained and the residual lactose and galactose contained thereof were determined as follows: whey sample was diluted in sulfuric acid solution, homogenized into liquid cheese and centrifuged. The supernatant was filtrated and injected on HPLC (high-performance-liquid-chromatography). Sugars were separated onto an $H^+$ ion exchange column (ROA Rezex®) 150 mm×7.8 mm×8 μm) column and detected with refractometer. Results of the HPLC measurements are summarized in Table 5.

TABLE 5 sugar concentrations in whey using different cultures with and without curd washing

| | Culture | Lactose (g/kg) | Galactose (g/kg) |
|---|---|---|---|
| Without curd washing | SWIFT14 | 40.71 | 0.43 |
| | ST Gal−, LL | 42.23 | 0.34 |
| | ST Gal−, LL, LH | 40.84 | 0.34 |
| | DSM32823 | 40.98 | 0.30 |
| | DSM32823, LL, LH | 41.75 | 0.30 |
| | MC70 | 41.86 | 0.26 |
| With curd washing (20%) | SWIFT14 | 32.34 | 0.40 |
| | ST Gal−, LL | 32.20 | 0.28 |
| | ST Gal−, LL, LH | 32.81 | 0.30 |
| | DSM32823 | 31.89 | 0.25 |
| | DSM32823, LL, LH | 32.67 | 0.23 |
| | MC70 | 32.86 | 0.20 |

A maximal value of 0.3 g/L of galactose in the whey after molding was considered to be the upper acceptable limit, for an optimal whey valorization at the industrial scale.

With curd washing, all the cultures (except SWIFT14) enabled to obtain a residual galactose in the whey after molding of at most 0.3 g/L. The best results were obtained with the MC70 culture (0.2) followed by the DSM32823-based cultures (0.23 and 0.25).

Without curd washing, only the MC70 culture (0.26) and the DSM32823-based cultures (0.30) enabled to obtain an acceptable galactose concentration in the whey.

Altogether, these data confirm not only the gain on galactose decrease in curd but also on galactose decrease in whey of:

- a combination of galactose-negative *S. thermophilus* and *Lactococcus lactis*, and optionally *Lactobacillus helveticus*; and
- cultures based on galactose-positive *S. thermophilus* selected as defined in the invention (assay I and/or assay II).

CONCLUSIONS

Results on time of manufacturing, galactose concentrations (in whey and curd) and browning are summarized in Table 6 below. They give an overview of the benefits of each tested culture for the cheese manufacturers (processing time and galactose in whey) and for the final consumers (browning).

Thus, the results obtained with SWIFT14 or MC70 show that the benefits are either in terms of time of manufacturing or in terms of browning, but none of these 2 cultures enables to reach both benefits for producers, pizza retailers and consumers.

In contrast, the use of cultures comprising both galactose-negative *S. thermophilus* and *Lactococcus lactis* stains, optionally in combination with a curd washing step, shows benefits in terms of time manufacturing and browning improvement, and possibly on galactose in whey, confirming the high interest for such cultures in manufacturing pasta filata cheese.

Finally, the use of cultures comprising a galactose-positive *S. thermophilus* as defined in the invention (such as DSM32823) shows benefits in terms of time manufacturing, galactose in whey and browning improvement (with or without curd washing), confirming the exceptional behavior of such type of strains in manufacturing pasta-filata cheese.

TABLE 6 summary of the use of the different cultures (with or without curd washing) on time of manufacturing, galactose concentrations and browning results.

| | Strain(s) | Time of manufacture (minutes) | residual galactose (g/kg) In whey after moulding | residual galactose (g/kg) in curd after stretching | browning results (L) |
|---|---|---|---|---|---|
| Without curd washing | SWIFT14 | 248 | 0.43 | 5.49 | 43 |
| | ST Gal−, LL | 248 | 0.34 | 3.57 | 59 |
| | ST Gal−, LL, LH | 248 | 0.34 | 3.86 | 64 |
| | DSM32823 | 250 | 0.30 | 2.03 | 64 |
| | DSM32823, LL, LH | 248 | 0.30 | 1.57 | 63 |
| | MC70 | 270 | 0.26 | 0.15 | 64 |
| With curd washing (20%) | SWIFT14 | 248 | 0.40 | 4.67 | 43 |
| | ST Gal−, LL | 248 | 0.28 | 3.44 | 57 |
| | ST Gal−, LL, LH | 248 | 0.30 | 3.77 | 61 |
| | DSM32823 | 250 | 0.25 | 1.46 | 69 |
| | DSM32823, LL, LH | 248 | 0.23 | 1.41 | 70 |
| | MC70 | 270 | 0.20 | 0.14 | 69 |

The invention claimed is:

1. A method to manufacture pasta-filata cheese, comprising:

a) providing or producing a curd, wherein said curd is obtained by inoculating and fermenting milk with at least a galactose-positive *Streptococcus thermophilus* strain being strain DSM32823 deposited at DSMZ on May 29, 2018 or a variant of the DSM32823 strain;

b) stretching the curd to obtain a stretched curd; and c) manipulating the stretched curd to finally end up with a pasta-filata cheese.

2. The method according to claim 1, wherein said curd has a pH comprised between 4.9 and 5.3 and/or a submicelle dimension from 5 nm to 15 nm.

3. The method according to claim 1, wherein the producing the curd comprises:

a1) inoculating milk with at least the galactose-positive *Streptococcus thermophilus* strain DSM32823 or the variant of the DSM32823 strain to obtain an inoculated milk;

a2) fermenting the inoculated milk to obtain a coagulated milk;

a3) cutting the coagulated milk, heating and stirring, to obtain a mix of curd and whey; and a4) draining the mix of curd and whey to obtain a curd.

4. The method according to claim 1, wherein the milk is further inoculated with a *Lactobacillus helveticus* strain.

5. The method according to claim 3, further comprising washing the curd, when heating and stirring at the step a3).

6. The method according to claim 1, further comprising milling the curd obtained by the step a) before the stretching of the step b).

7. The method according to claim 3, wherein a process time between milk inoculation and a time a curd is obtained is between 3.5 and 5 hours.

* * * * *